United States Patent
Shaver et al.

(10) Patent No.: US 12,080,380 B2
(45) Date of Patent: Sep. 3, 2024

(54) IMPLEMENTING A GENERATIVE MACHINE LEARNING ARCHITECTURE TO PRODUCE TRAINING DATA FOR A CLASSIFICATION MODEL

(71) Applicant: Just-Evotec Biologics, Inc., Seattle, WA (US)

(72) Inventors: Jeremy Martin Shaver, Lake Forest Park, WA (US); Tileli Amimeur, Seattle, WA (US); Randal Robert Ketchem, Snohomish, WA (US); Joshua Smith, Seattle, WA (US)

(73) Assignee: Just-Evotec Biologics, Inc., Seattle, WA (US)

( * ) Notice: Subject to any disclaimer, the term of this patent is extended or adjusted under 35 U.S.C. 154(b) by 0 days.

(21) Appl. No.: 18/043,528

(22) PCT Filed: Aug. 27, 2021

(86) PCT No.: PCT/US2021/047939
§ 371 (c)(1),
(2) Date: Feb. 28, 2023

(87) PCT Pub. No.: WO2022/047150
PCT Pub. Date: Mar. 3, 2022

(65) Prior Publication Data
US 2023/0253067 A1    Aug. 10, 2023

Related U.S. Application Data

(60) Provisional application No. 63/071,738, filed on Aug. 28, 2020.

(51) Int. Cl.
| | |
|---|---|
| *G01N 33/48* | (2006.01) |
| *G06N 3/08* | (2023.01) |
| *G16B 5/20* | (2019.01) |
| *G16B 15/20* | (2019.01) |
| *G16B 15/30* | (2019.01) |
| *G16B 40/00* | (2019.01) |
| *G16B 40/20* | (2019.01) |

(52) U.S. Cl.
CPC .............. *G16B 15/30* (2019.02); *G06N 3/08* (2013.01); *G16B 5/20* (2019.02); *G16B 15/20* (2019.02); *G16B 40/00* (2019.02); *G16B 40/20* (2019.02)

(58) Field of Classification Search
None
See application file for complete search history.

(56) References Cited

U.S. PATENT DOCUMENTS

2019/0259474 A1    8/2019    Wang et al.

FOREIGN PATENT DOCUMENTS

| | | |
|---|---|---|
| CN | 111462815 A | 7/2020 |
| WO | WO-2019097014 A1 | 5/2019 |
| WO | WO-2020167667 A1 | 8/2020 |
| WO | WO-2022047150 A1 | 3/2022 |

OTHER PUBLICATIONS

Gui, Jie, et al. "A review on generative adversarial networks: Algorithms, theory, and applications." IEEE transactions on knowledge and data engineering 35.4 (2021): 3313-3332.*
Wan, Cen, and David T. Jones. "Protein function prediction is improved by creating synthetic feature samples with generative adversarial networks." Nature Machine Intelligence 2.9 (2020): 540-550.*
Yang, Hang, et al. "GANcon: protein contact map prediction with deep generative adversarial network." IEEE Access 8 (2020): 80899-80907.*
Repecka, Donatas, et al. "Expanding functional protein sequence spaces using generative adversarial networks." Nature Machine Intelligence 3.4 (2021): 324-333.*
"A Friendly Introduction to Generative Adversarial Networks (GANs)," Serrano.Academy, May 5, 2020. Retrieved from the Internet <URL:https://youtu.be/8L11aMN5KY8?si=5Ta2sIPMOBtmy6xF>.*
"International Application Serial No. PCT/US2021/047939, International Search Report mailed Dec. 13, 2021", 2 pgs.
"International Application Serial No. PCT/US2021/047939, Written Opinion mailed Dec. 13, 2021", 5 pgs.
"International Application Serial No. PCT/US2021/047939, International Preliminary Report on Patentability mailed Mar. 9, 2023", 7 pgs.
"European Application Serial No. 21862817.0, Extended European Search Report mailed Jan. 22, 2024", 16 pgs.
Amimeur, T, et al., "Designing Feature-Controlled Humanoid Antibody Discovery Libraries Using Generative Adversarial Networks", bioRxiv., 2020.04.12.024844 Retrieved from the Internet: <URL:https://www.biorxiv.org/content/10.1101/2020.04.12.024844v1.full.pdf>, (Apr. 23, 2020), 1-35.
Creswell, Antonia, et al., "Generative Adversarial Networks: An Overview", IEEE Signal Processing Magazine 35.1, (2018), 53-65.

\* cited by examiner

*Primary Examiner* — Anna Skibinsky
(74) *Attorney, Agent, or Firm* — Schwegman Lundberg & Woessner, P.A.

(57) ABSTRACT

Amino acid sequences of proteins can be produced using one or more generative machine learning architectures. The amino acid sequences produced by the one or more generative machine learning architectures can be used to train a classification model architecture. The classification model architecture can classify amino acid sequences according to a number of classifications. Individual classifications of the number of classifications can correspond to at least one of a structural feature of proteins, a range of values of a structural feature of proteins, a biophysical property of proteins, or a range of values of a biophysical property of proteins.

20 Claims, 8 Drawing Sheets

IMPLEMENTING A GENERATIVE MACHINE LEARNING ARCHITECTURE TO PRODUCE TRAINING DATA FOR A CLASSIFICATION MODEL

CROSS-REFERENCE TO RELATED APPLICATION(S) AND PRIORITY CLAIM

This application is a U.S. national stage filing under 35 U.S.C. 371 from International Application No. PCT/US2021/047939, filed on 27 Aug. 2021, and published as WO 2022/047150 A1 on 3 Mar. 2022, which claims priority to U.S. Provisional Application No. 63/071,738 filed on 28 Aug. 2020 and entitled "Implementing a Generative Machine Learning Architecture to Produce Training Data for a Classification Model," the entirety of which are incorporated herein by reference.

BACKGROUND

Proteins are biological molecules that are comprised of one or more chains of amino acids. Proteins can have various functions within an organism. For example, some proteins can be involved in causing a reaction to take place within an organism. In other examples, proteins can transport molecules throughout the organism. In still other examples, proteins can be involved in the replication of genes. Additionally, some proteins can have therapeutic properties and be used to treat various biological conditions. The structure and function of proteins are based on the arrangement of amino acids that comprise the proteins. The arrangement of amino acids for proteins can be represented by a sequence of letters with each letter corresponding to an amino acid at a respective position. The arrangement of amino acids for proteins can also be represented by three dimensional structures that not only indicate the amino acids at various locations of the protein, but also indicate three dimensional features of the proteins, such as an α-helix or a β-sheet.

BRIEF DESCRIPTION OF THE DRAWINGS

The present disclosure is illustrated by way of example and not limitation in the figures of the accompanying drawings, in which like references indicate similar elements.

DETAILED DESCRIPTION

Figure 1:
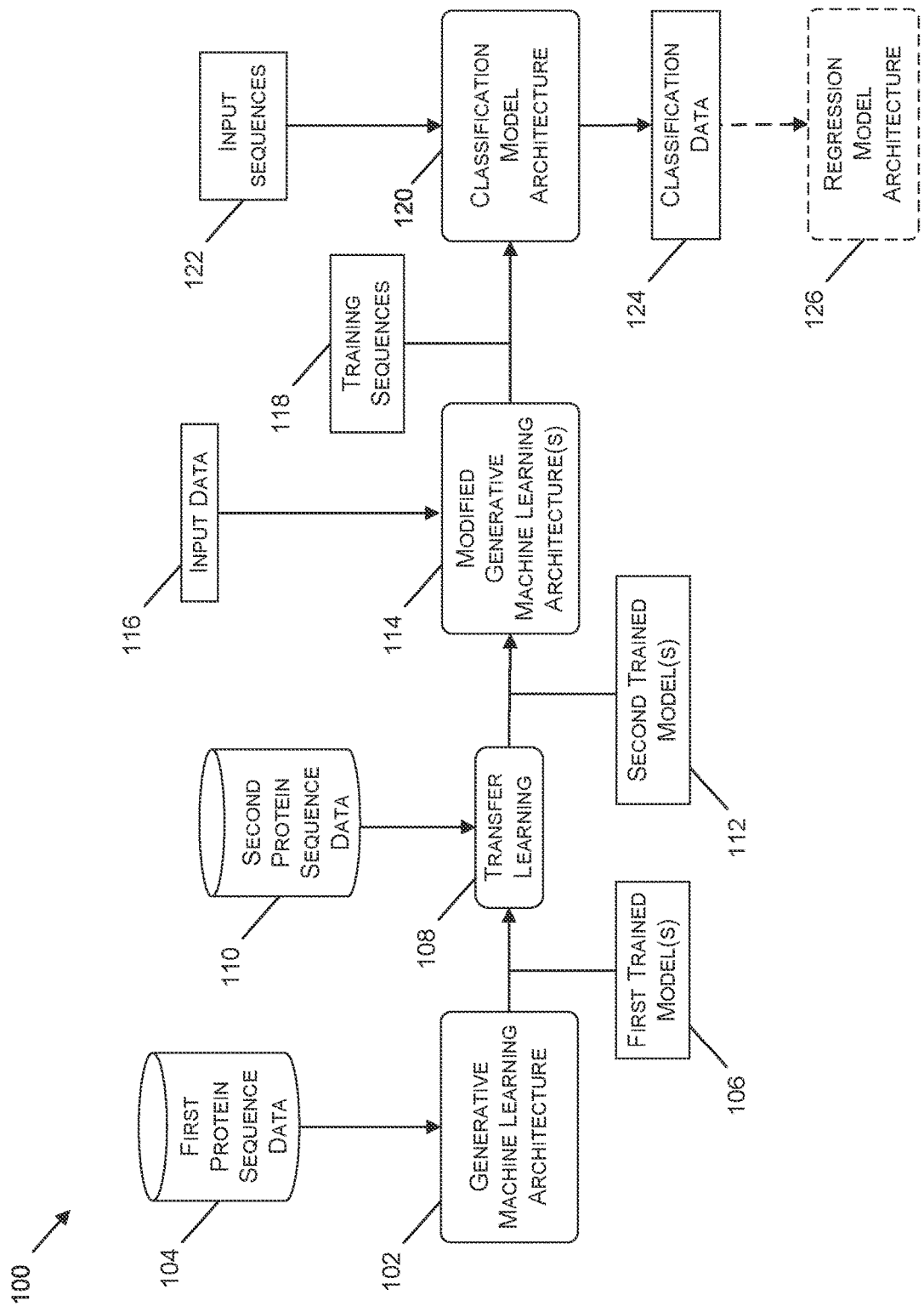
FIG. 1 is a diagram illustrating an example framework to train a classification model using amino acid sequences produced by a generative machine learning architecture, in accordance with some one or more implementations.

Proteins can have many beneficial uses within organisms. In particular situations, proteins can be used to treat diseases and other biological conditions that can detrimentally impact the health of humans and other mammals. In various scenarios, proteins can participate in reactions that are beneficial to subjects and that can counteract one or more biological conditions being experienced by the subjects. In one or more examples, proteins can also hind to target molecules within an organism that may be detrimental to the health of a subject. For these reasons, many individuals and organizations have sought to develop proteins that may have therapeutic benefits.

The development of proteins can be a time consuming and resource intensive process. Often, candidate proteins for development can be identified as potentially having various biophysical properties, structural features (e.g., negatively charged patches, hydrophobic patches), three-dimensional (3D) structures, and/or behavior within an organism. In order to determine whether the candidate proteins actually have the desired characteristics, the proteins can be synthesized and then tested to determine whether the actual characteristics of the synthesized proteins correspond to the desired characteristics. Due to the amount of resources needed to synthesize and test proteins for specified biophysical properties, structural features, 3D structures, and/or behaviors, the number of candidate proteins synthesized for therapeutic purposes is limited. In one or more situations, the number of proteins synthesized for therapeutic purposes can be limited by the loss of resources that takes place when candidate proteins are synthesized and do not have the desired characteristics. As used herein, structural features of proteins can refer to features of one or more amino acids or features of one or more groups of amino acids included in a protein molecule.

Additionally, existing techniques that classify amino acid sequences with regard to structural features rely on large numbers of amino acid sequences for training because these existing techniques use a large number of calculations related to structural feature classification. For example, existing techniques may follow first principles-based approaches that analyze each atom or cluster of atoms in a protein to determine whether a structural feature is present in a protein. Due to the large amount of computational resources needed to determine structural features using first principles-based techniques, previous systems typically made assumptions about the behavior of atoms or groups of atoms of proteins. These assumptions can lead to inaccuracies in the classification of proteins based on structural features.

Inferential modeling techniques can provide an alternative to the existing first principles-based techniques that are used to classify proteins based on structural features. However, the training of inferential modeling techniques can utilize hundreds of thousands up to millions of protein sequences. Conventional techniques that can be used to generate amino acid sequences for the training of inferential models can be limited in their scope and accuracy. In various situations, previous computer-implemented techniques to generate protein sequences can be limited by the amount of data available and/or the types of data available that may be needed by those previous techniques to accurately generate protein sequences with specified characteristics. Additionally, the techniques utilized to produce models that can generate protein sequences with particular characteristics can be complex and the know-how needed to produce models that are accurate and efficient is not readily available. In one or more scenarios, the length of the protein sequences produced by existing models can also be limited because the accuracy of existing techniques can decrease as the lengths of the proteins increases. Thus, the number of amino acid sequences of proteins that can be accurately and efficiently generated by previously utilized techniques is often limited.

The techniques, methods, and systems described herein can be used to classify amino acid sequences of proteins with inferential modeling techniques. Inferential models can be training using amino acid sequences produced by generative machine learning architectures. The generative machine learning architectures can include generative adversarial networks. In addition, the amino acid sequences of the proteins used to train the inferential models can be produced by other generative machine learning architectures, such as autoencoders. In various examples, multiple generating components of one or more generative adversarial networks can be used to produce amino acid sequences to train inferential models that classify amino acid sequences based on structural features.

In one or more examples, an initial version of a generating component of a generative machine learning architecture can be trained to generate amino acid sequences of proteins without regard to specific structural features of the proteins. The generating component can then be trained further using datasets of proteins that have one or more specified structural features. For example, the initial version of the generating component can be trained using a first dataset of proteins to produce a first modified version of the generating component. The first dataset can include amino acid sequences of proteins having at least one hydrophobic region with a first range of sizes, where the size of a hydrophobic region corresponds to a number of amino acids that are included in the hydrophobic region. In various examples, the size of a hydrophobic region can correspond to a number of exposed amino acids that are included in the hydrophobic region. In various examples, an exposed amino acid can include an amino acid that is located on a protein such that the amino acid is available to interact with molecules other than the protein. After being trained, the first modified version of the generating component can produce first amino acid sequences that have at least a threshold probability of having at least one hydrophobic region included in the first range of sizes. Additionally, the initial version of the generating component can be trained using a second dataset of proteins to produce a second modified version of the generating component. The second dataset can include amino acid sequences of proteins having at least one hydrophobic region with a second range of sizes that are different from the first range of sizes. To illustrate, the first dataset can correspond to hydrophobic regions that are relatively small, and the second dataset can correspond to hydrophobic regions that are relatively large. Subsequent to the training process with the second dataset, the second modified version of the generating component can produce second amino acid sequences that have at least a threshold probability of having at least one hydrophobic region included in the second range of sizes.

In various examples, the first amino acid sequences can be provided to an inferential model architecture as first training data corresponding to examples of amino acid sequences having at least one hydrophobic region included in the first range of sizes. The second amino acid sequences can be provided to the inferential model architecture as second training data corresponding to examples of amino acid sequences having at least one hydrophobic region included in the second range of sizes. In this way, the inferential modeling architecture can be trained to distinguish between amino acid sequences of proteins that have hydrophobic regions corresponding to the first range of sizes and amino acid sequences of proteins that have hydrophobic regions corresponding to the second range of sizes. Accordingly, the trained inferential modeling architecture can classify a given protein based on its amino acid sequence as having a hydrophobic region included in the first range of sizes or a hydrophobic region included in the second range of sizes.

By implementing an inferential modeling architecture to classify amino acid sequences according to structural properties of proteins, the techniques, methods, frameworks, and systems described herein reduce the amount of computational calculation and computational resources used to perform the classification in relation to existing systems and frameworks. Additionally, the use of generative machine learning architectures to produce training data for the inferential models can provide a level of specificity, quantity, and accuracy of amino acid sequences to effectively train the inferential models that is not found in conventional systems and techniques.

FIG. 1 is a diagram illustrating an example framework 100 to train a classification model using amino acid sequences produced by a generative machine learning architecture, in accordance with one or more implementations. The framework 100 can include a generative machine learning architecture 102. The generative machine learning architecture 102 can implement one or more models to generate amino acid sequences. The amino acid sequences produced by the generative machine learning architecture 102 can correspond to proteins. In one or more examples, the sequences produced by the generative machine learning architecture 102 can include amino acid sequences of antibodies. In various implementations, the one or more models implemented by the generative machine learning architecture 102 can include one or more functions.

In one or more implementations, the generative machine learning architecture 102 can implement one or more neural network technologies. For example, the generative machine learning architecture 102 can implement one or more recurrent neural networks. Additionally, the generative machine learning architecture 102 can implement one or more convolutional neural networks. Further, the machine learning architecture 102 can implement a combination of recurrent neural networks and convolutional neural networks. In one or more examples, the generative machine learning architecture 102 can include one or more generative adversarial networks (GANs). In these situations, the generative machine learning architecture 102 can include a generating component that produces amino acid sequences and a challenging component that evaluates the amino acid sequences produced by the generating component with respect to a training dataset. In further examples, the generative machine learning architecture 102 can include one or more autoencoders. In these implementations, the generative machine learning architecture 102 can include at least one of an encoder or a decoder. In one or more illustrative examples, the generative machine learning architecture 102 can include a variational autoencoder.

First protein sequence data 104 can include a number of amino acid sequences that can be used in the training of the generative machine learning architecture 102. The first protein sequence data 104 can include sequences obtained from one or more data sources that store protein amino acid sequences. The first protein sequence data 104 can include amino acid sequences of one or more proteins. In various examples, the first protein sequence data 104 can include amino acid sequences of portions of one or more proteins. In one or more illustrative examples, the first protein sequence data 104 can include amino acid sequences of fibronectin type III (FNIII) proteins, avimers, antibodies, VHH domains, kinases, zinc fingers, combinations thereof, and the like. In one or more additional examples, the first protein sequence data 104 can include amino acid sequences of portions of antibodies, such as at least a portion of one or more complementarity determining regions (CDRs) of antibodies, at least a portion of one or more light chains of antibodies, at least a portion of one or more heavy chains of antibodies, at least a portion of one or more variable regions of antibodies, at least a portion of one or more constant regions of antibodies, at least a portion of one or more hinge regions of antibodies, at least a portion of one or more antigen binding regions of antibodies, one or more combinations thereof, and so forth.

In one or more implementations, the amino acid sequences included in the first protein sequence data 104 used to train the generative machine learning architecture 102 can impact the amino acid sequences produced by the generative machine learning architecture 102. For example, the characteristics, biophysical properties, manufacturing characteristics (e.g., titer, yield, etc.) and so forth, of the first protein sequence data 104 can impact characteristics, biophysical properties, and/or manufacturing characteristics of the amino acid sequences produced by the generative machine learning architecture 102. To illustrate, in situations where antibodies are included in the first protein sequence data 104 provided to the generative machine learning architecture 102, the amino acid sequences produced by the generative machine learning architecture 102 can correspond to antibody amino acid sequences. In one or more examples, in scenarios where T-cell receptors are included in the first protein sequence data 104 provided to the generative machine learning architecture 102, the amino acid sequences produced by the generative machine learning architecture 102 can correspond to T-cell receptor amino acid sequences. In one or more additional examples, in situations where kinases are included in the first protein sequence data 104, the amino acid sequences produced by the generative machine learning architecture 102 can correspond to amino acid sequences of kinases. In various implementations where amino acid sequences of a variety of different types of proteins are included in the first protein sequence data 104, the generative machine learning architecture 102 can generate amino acid sequences having characteristics of proteins generally and may not correspond to a particular type of protein.

During the training process, the generative machine learning architecture 102 can analyze amino acid sequences produced by the generative machine learning architecture 102 with respect to the training sequences included in the first protein sequence data 104 to evaluate a loss function of the generative machine learning architecture 102. In one or more examples, output of the loss function can be used to modify the sequences generated by the generative machine learning architecture 102. For example, output related to the loss function can be used to modify one or more components of the generative machine learning architecture 102, such as an encoder, a decoder, and/or a generator of a generative adversarial network, to produce amino acid sequences that correspond more closely to amino acid sequences included in the first protein sequence data 104. In one or more examples, components of the generative machine learning architecture 102 may be modified to minimize the loss function.

After the generative machine learning architecture 102 has undergone a training process, one or more first trained models 106 can be generated that can produce amino acid sequences of proteins. The one or more first trained models 106 can include one or more components of the generative machine learning architecture 102 after a training process using the first protein sequence data 104. In one or more implementations, the one or more first trained models 106 can include a generator of a generative adversarial network that has been trained using the first protein sequence data 104. Additionally, the one or more trained models 106 can include at least one of an encoder or a decoder of an autoencoder of the generative machine learning architecture 102 that has been trained using the first protein sequence data 104.

In one or more examples, the training process for the generative machine learning architecture 102 can be complete after the function(s) implemented by one or more components of the generative machine learning architecture 102 converge. The convergence of a function can be based on the movement of values of model parameters toward particular values as protein sequences are generated by one or more components of the generative machine learning architecture 102 and feedback is obtained in relation to at least one loss function based on differences between the amino acid sequences included in the first protein sequence data 104 and the amino acid sequences generated by the generative machine learning architecture 102.

In various implementations, the training of the generative machine learning architecture 102 can be complete when the protein sequences produced by the generative machine learning architecture 102 have particular characteristics. To illustrate, the amino acid sequences generated by the generative machine learning architecture 102 can be analyzed by one or more software tools that can analyze amino acid sequences to determine at least one of biophysical properties of the amino acid sequences, structural features of the amino acid sequences, or adherence to amino acid sequences corresponding to one or more protein germlines. As used herein, germline, can correspond to amino acid sequences of proteins that are conserved when cells of the proteins replicate. An amino acid sequence can be conserved from a parent cell to a progeny cell when the amino acid sequence of the progeny cell has at least a threshold amount of identity with respect to the corresponding amino acid sequence in the parent cell. In one or more illustrative examples, a portion of an amino acid sequence of a human antibody that is part of a kappa light chain that is conserved from a parent cell to a progeny cell can be a germline portion of the antibody.

In one or more implementations, the analysis of amino acid sequences can be used to determine whether training of the generative machine learning architecture 102 is to cease or to continue. For example, the software tool can determine that less than a threshold amount of amino acid sequences produced by the generative machine learning architecture 102 have one or more specified characteristics. In these scenarios, the training of the generative machine learning architecture 102 may continue. Additionally, in situations where the software tool determines that a threshold amount of amino acid sequences produced by the generative machine learning architecture 102 do correspond to one or more specified characteristics, the training of the generative machine learning architecture 102 can stop.

The one or more first trained models 106 can undergo transfer learning at 108 based on second protein sequence data 110. The transfer learning that is performed at 108 can modify the one or more first trained models 106 based on the amino acid sequences included in the second protein sequence data 110. The transfer learning that is performed at 108 can produce one or more second trained models 112 that are modified versions of the one or more first trained models 106. In various examples, the transfer learning that takes place at 108 can include an additional training process of the one or more first trained models 106 using training data obtained from the second protein sequence data 110. By using a training dataset to produce the second trained models 112 that is different from the training dataset used to produce the first trained models 106, the second trained models 112 can produce amino acid sequences that can have some general characteristics that correspond to the amino acid sequences included in the first protein sequence data 104 and that also have one or more specified characteristics that correspond to features of the proteins related to the amino acid sequences included in the second protein sequence data 110. In one or more examples, the number of amino acid sequences included in at least one of the first protein sequence data 104 or the second protein sequence data 110 can be in the thousands of amino acid sequences up to tens of thousands of amino acid sequences or more.

In various implementations, the one or more first trained models 106 can be trained to produce the one or more second trained models 112 in a manner that is similar to the training of the generative machine learning architecture 102 that produced the one or more first trained models 106. In one or more examples, components of the one or more first trained models 106 may be modified to minimize at least one loss function. Additionally, the training process for the one or more first trained models 106 used to produce the one or more second trained models 112 can be complete after one or more functions implemented by one or more components of the one or more first trained models 106 converge. In one or more further examples, the training process used to generate the one or more second trained models 112 from the one or more first trained models 106 can be complete based on an analysis of a software tool indicating that amino acid sequences produced using the one or more second trained models 112 corresponds to one or more specified criteria. The one or more specified criteria can correspond to at least one of one or more structural features of proteins having amino acid sequences produced by the one or more second trained models 112 or one or more biophysical properties of proteins having amino acid sequences produced by the one or more second trained models 112.

In one or more examples, the second protein sequence data 110 can include amino acid sequences of proteins that have features that are different from the features of the proteins related to the first protein sequence data 104. In various examples, the second protein sequence data 110 can include a subset of the amino acid sequences included in the first protein sequence data 104. In one or more additional examples, the second protein sequence data 110 can include a greater number of a group of amino acid sequences having one or more specified characteristics in relation to the number of amino acid sequences having the one or more specified characteristics included in the first protein sequence data 104. For example, the first protein sequence data 104 can include amino acid sequences of proteins having a variety of structural features. To illustrate, the first protein sequence data 104 can include a number of amino acid sequences of proteins having various sizes of hydrophobic regions, a number of amino acid sequences of proteins having various sizes of negatively charged regions, a number of amino acid sequences of proteins having various sizes of positively charged regions, a number of amino acid sequences of proteins various sizes of polar regions, one or more combinations thereof, and the like. Additionally, the second protein sequence data 110 can include a greater number of amino acid sequences of proteins that have hydrophobic regions with a specified range of sizes than the number of amino acid sequences included in the first protein sequence data 104 that have the hydrophobic regions with the specified range of sizes. In these scenarios, the second trained models 112 can primarily produce amino acid sequences of proteins having hydrophobic regions with the specified range of sizes. In one or more further examples, the second protein sequence data 110 can include a greater number of amino acid sequences of proteins that have negatively charged regions with a specified range of sizes than the number of amino acid sequences included in the first protein sequence data 104 that have negatively charged regions with the specified range of sizes. In these situations, the one or more second trained models 112 can primarily produce amino acid sequences of proteins having negatively charged regions with the specified range of sizes.

In one or more implementations, the amino acid sequences included in the second protein sequence data 110 can include a filtered set of amino acid sequences. For example, a set of amino acid sequences can be evaluated according to one or more criteria. In various examples, at least one of one or more software tools, one or more diagnostic tools, or one or more analytical instruments can be used to identify amino acid sequences included in the set of amino acid sequences that correspond to the one or more criteria. The amino acid sequences that satisfy the one or more criteria can then be added to the second protein sequence data 110. In one or more illustrative examples, a number of amino acid sequences can be evaluated to identify proteins having at least one polar region for inclusion in the second protein sequence data 110 that can be used to modify the one or more first trained models 106 to produce the one or more second trained models 112. In one or more additional illustrative examples, a number of amino acid sequences can be evaluated to identify proteins including at least one positively charged region having a specified range of sizes for inclusion in the second protein sequence data 110 that can be used to modify the one or more first trained models 106 to produce the one or more second trained models 112.

In one or more illustrative examples, the transfer learning at 108 can modify a first distribution of proteins having one or more characteristics produced by the one or more first trained models 106 such that a second distribution of proteins having the one or more characteristics produced by the one or more second trained models 112 is different from the first distribution. For example, the one or more first trained models 106 may produce proteins having at least one hydrophobic region included in a first range of sizes, such as from about 1 amino acid to about 15 amino acids with an average size of 7 amino acids and a standard deviation of 1.5 amino acids. Additionally, the one or more second trained models 112 may produce proteins having at least one hydrophobic region includes in a second range of sizes, such as from about 9 amino acids to about 15 amino acids with an average size of 12 amino acids and a standard deviation of 0.5 amino acids. In these scenarios, the second protein sequence data 110 can include amino acid sequences of proteins having at least one hydrophobic region that corresponds to the second range of sizes. In one or more additional examples, a probability of the one or more first trained models 106 generating proteins having one or more characteristics can be different from a probability of the one or more second trained models 112 generating proteins having the one or more characteristics. To illustrate, the one or more first trained models 106 may have from about a 10% probability to about a 15% probability of generating amino acid sequences of proteins having at least one negatively charged region with no greater than 5 amino acids, while the one or more second trained models 112 may have from about a 95% probability to about a 99% probability of generating amino acid sequences of proteins having at least one negatively charged region with no greater than 5 amino acids. In these situations, the second protein sequence data 110 can include amino acid sequences of proteins having at least one negatively charged patch with a size that is no greater than 5 amino acids.

The one or more second trained models 112 can be included in one or more modified generative machine learning architectures 114. In one or more examples, the one or more modified generative machine learning architectures 114 can include one or more generative adversarial networks. In these situations, the one or more second trained models 112 can operate as one or more generating components of the one or more generative adversarial networks. In addition, the one or more modified generative machine learning architectures 114 can include one or more autoencoders. In these scenarios, the one or more second trained models 112 can operate as at least one of one or more encoders or one or more decoders of the one or more autoencoders.

The one or more modified generative machine learning architectures 114 can generate amino acid sequences based on input data 116. In one or more examples, the input data 116 can include a random or pseudo-random series of numbers that can be used by one or more generative adversarial networks included in the one or more modified generative machine learning architectures 114 to produce amino acid sequences. Additionally, in implementations where the one or more modified generative machine learning architectures 114 include one or more autoencoders, the input data 116 can include an input sample that is provided to a decoder in conjunction with an encoding produced by an encoder and the decoder can use the input sample to produce a number of amino acid sequences.

In various examples, the one or more modified generative machine learning architectures 114 can include a plurality of generative machine learning architectures with individual generative machine learning architectures producing sequences of amino acids that correspond to proteins that have one or more specified structural features. For example, the one or more modified generative machine learning architectures 114 can include a first generative machine learning architecture that produces amino acid sequences that correspond to proteins having hydrophobic patches with a first range of sizes, a second generative machine learning architecture that produces amino acid sequences that correspond to proteins having hydrophobic patches with a second range of sizes, and a third generative machine learning architecture that produces amino acid sequences that correspond to proteins having hydrophobic patches with a third range of sizes. In one or more examples, there may be some overlap between the sizes of hydrophobic patches included in the first range of sizes and the second range of sizes and between sizes of hydrophobic patches included in the second range of sizes and the third range of sizes.

The amino acid sequences generated by the one or more modified generative machine learning architectures 114 can include training sequences 118 that can be used to train a classification model architecture 120. The classification model architecture 120 can determine a classification for input sequences 122. In various examples, the classification model architecture 120 can implement one or more inferential modeling techniques. The one or more inferential modeling techniques can include at least one of one or more p-value techniques, one or more confidence interval techniques, one or more null hypothesis techniques, one or more Bayesian inference techniques, one or more frequentist inference techniques, one or more likelihood-based inference techniques, one or more Akaike information criterion (AIC) techniques, one or more minimum description length techniques, or one or more structural inference techniques, and the like. In one or more additional examples, the classification model architecture 120 can include at least one of one or more logistic regression techniques, one or Naïve Bayes techniques, one or more stochastic gradient descent techniques, one or more K-nearest neighbors techniques, one or more decision tree techniques, one or more random forest techniques, or one or more support vector machine techniques.

The input sequences 122 can include amino acid sequences of proteins that are to be classified by the classification model architecture 120. For example, the classification model architecture 120 can identify amino acid sequences included in the input sequences 122 that correspond to a plurality of classifications of proteins. In one or more examples, the classification model architecture 120 can identify amino acid sequences that correspond to proteins having one or more structural features. For example, the classification model architecture 120 can differentiate between amino acid sequences of a first group of proteins having one or more first characteristics and amino acid sequences of a second group of proteins having one or more second characteristics that are different from the one or more first characteristics. In one or more illustrative examples, the classification model architecture 120 can classify a first number of amino acid sequences included in the input sequences 122 as having at least a threshold probability of including one or more polar regions with a first range of sizes and the classification model architecture 120 can classify a second number of amino acid sequences included in the input sequences 122 as having at least a threshold probability of including one or more polar regions with a second range of sizes that is different from the first range of sizes. In one or more additional illustrative examples, the classification model architecture 120 can classify a first group of amino acid sequences included in the input sequences 122 as antibodies having at least a threshold probability of including one or more negatively charged regions and the classification model architecture 120 can classify a second group of amino acid sequences included in the input sequences 122 as antibodies having at least a threshold probability of including one or more hydrophobic regions.

The output produced by the classification model architecture 120 can include classification data 124. The classification data 124 can indicate one or more classifications for individual amino acid sequences included in the input sequences 122. The classification data 124 can also indicate one or more classifications for groups of amino acid sequences included in the input sequences 122. In one or more examples, the classification data 124 can indicate a first number of amino acid sequences included in the input sequences 122 having a first classification and a second number of amino acid sequences included in the input sequences 122 having a second classification. The classification data 124 can correspond to a prediction for one or more classifications with respect to individual amino acid sequence included in the input sequences 122. For example, the classification data 124 for a given amino acid sequence included in the input sequences 122 can indicate a probability of the amino acid sequence having a given classification. In various examples, the classification data 124 can indicate a plurality of probabilities for an amino acid sequence included in the input sequences 122 with respect to a plurality of classifications. In one or more illustrative examples, the classification data 124 can indicate a first probability of an amino acid sequence included in the input sequences 122 having a first classification and a second probability of the amino acid sequence having a second classification.

In at least some instances, the classification data 124 can be provided to a regression model architecture 126. The regression model architecture 126 can implement one or more regression techniques, such as at least one of one or more linear regression techniques, one or more logistic regression techniques, one or more ridge regression techniques, one or more Lasso regression techniques, one or more polynomial regression techniques, or one or more Bayesian linear regression techniques, and the like. In one or more examples, the regression model architecture 126 can determine one or more characteristics of proteins based on one or more classifications of the proteins indicated by the classification data 124. For example, the classification data 124 can indicate one or more structural features of one or more proteins and the regression model architecture 126 can determine one or more biophysical properties of the one or more proteins based on the one or more structural features indicated by the classification data 124. In one or more illustrative examples, the regression model architecture 126 can determine a measure of stability for amino acid sequences of proteins based on one or more classifications of the proteins indicated by the classification data 124. In one or more additional illustrative examples, the regression model architecture 126 can determine a measure of solubility for amino acid sequences of proteins based on one or more classifications of the proteins indicated by the classification data 124. In one or more further illustrative examples, the regression model architecture 126 can determine one or more biophysical properties that correspond to measures related to the manufacturing and/or downstream processing of the proteins.

Figure 2:
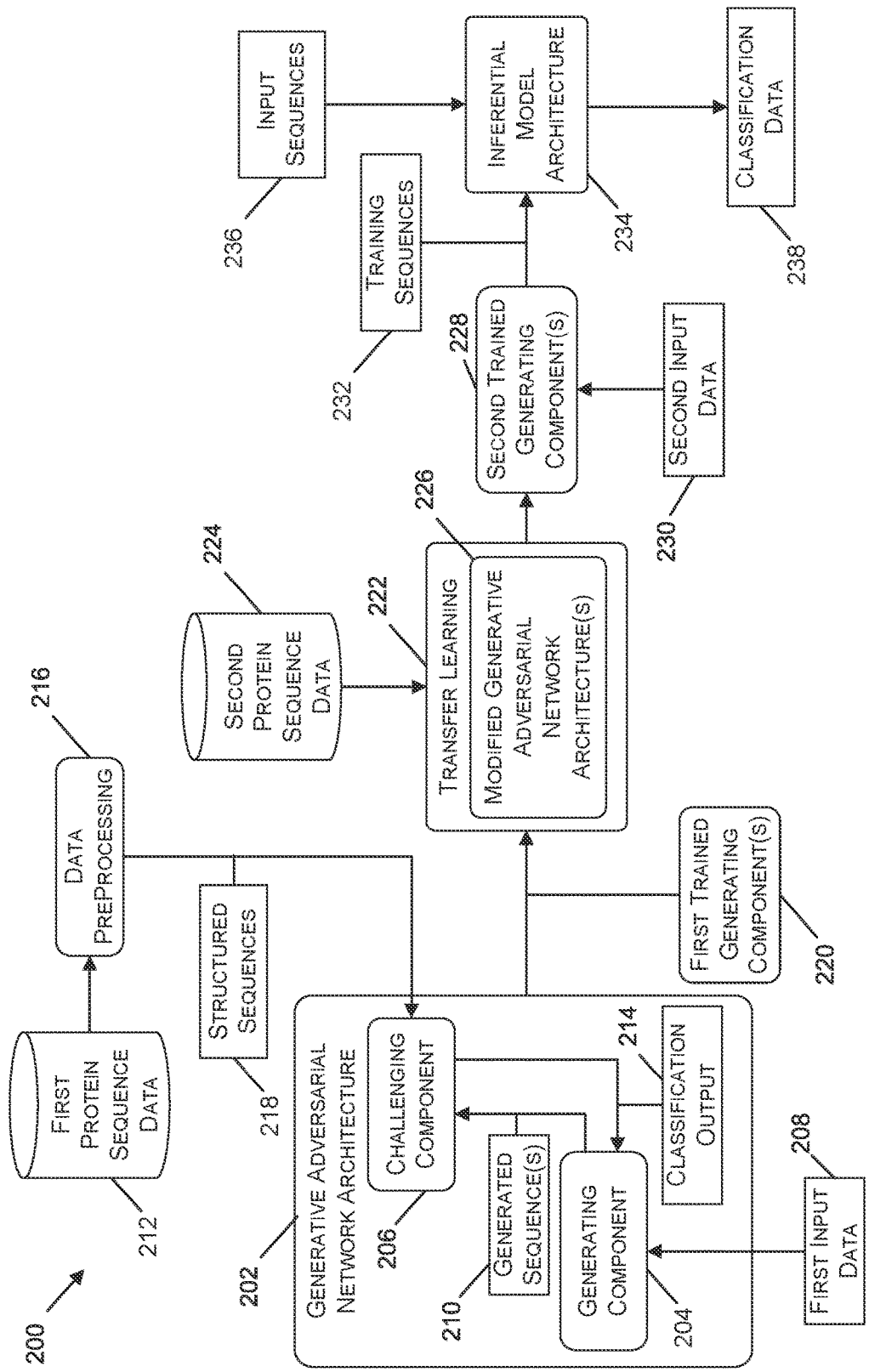
FIG. 2 is a diagram illustrating an example framework that includes one or more generative adversarial networks that produce amino acid sequences for training an inferential model, in accordance with one or more implementations.

FIG. 2 is a diagram illustrating an example framework 200 that includes one or more generative adversarial networks that produce amino acid sequences for training an inferential model, in accordance with one or more implementations. The framework 200 can include a generative adversarial network architecture 202. The generative adversarial network architecture 202 can include a generating component 204 and a challenging component 206. The generating component 204 can implement one or more models to generate amino acid sequences based on input provided to the generating component 204. In various implementations, the one or more models implemented by the generating component 204 can include one or more functions. The challenging component 206 can generate output indicating whether the amino acid sequences produced by the generating component 204 correspond to various characteristics. The output produced by the challenging component 206 can be provided to the generating component 204 and the one or more models implemented by the generating component 204 can be modified based on the feedback provided by the challenging component 206. In various implementations, the challenging component 206 can analyze the amino acid sequences generated by the generating component 204 with amino acid sequences of proteins included in training data and generate an output indicating an amount of correspondence between the amino acid sequences produced by the generating component 204 and the amino acid sequences of proteins provided to the challenging component 206 as training data. In one or more illustrative examples, the analysis performed by the challenging component 206 with respect to the amino acid sequences produced by the generating component 204 can include a comparison between the amino acid sequences included in the training data and the amino acid sequences produced by the generating component 204.

In various implementations, the generative adversarial network architecture 202 can implement one or more neural network technologies. For example, the generative adversarial network architecture 202 can implement one or more recurrent neural networks. Additionally, the generative adversarial network architecture 202 can implement one or more convolutional neural networks. In one or more implementations, the generative adversarial network architecture 202 can implement a combination of recurrent neural networks and convolutional neural networks. In one or more additional examples, the generating component 204 can include a generator and the challenging component 206 can include a discriminator. In one or more further implementations, the generative adversarial network architecture 202 can include a Wasserstein generative adversarial network (wGAN). In these scenarios, the generating component 204 can include a generator and the challenging component 206 can include a critic.

In the illustrative example of FIG. 2, an input vector 208 can be provided to the generating component 204 and the generating component 204 can produce one or more generated sequences 210 from the input vector 208 using one or more models. In one or more implementations, the input vector 208 can include noise data that is generated by a random number generator or a pseudo-random number generator. The generated sequence(s) 210 can be compared by the challenging component 206 against sequences of proteins included in first protein sequence data 212 that have been structured according to one or more schemas. The first protein sequence data 212 can include sequences of proteins obtained from one or more data sources that store protein sequences. The first protein sequence data 212 can be training data for the generative adversarial network architecture 202.

Based on similarities and/or differences between the generated sequence(s) 210 and the sequences obtained from the first protein sequence data 212, the challenging component 206 can generate a classification output 214 that indicates an amount of similarity and/or an amount of difference between the generated sequence 210 and sequences included in the first protein sequence data 212. In one or more examples, the challenging component 206 can label the generated sequence(s) 210 as zero and the sequences obtained from the first protein sequence data 212 as one. In these situations, the classification output 214 can correspond to a number from 0 and 1. In additional examples, the challenging component 206 can implement a distance function that produces an output that indicates an amount of distance between the generated sequence(s) 210 and the proteins included in the first protein sequence data 212. In these scenarios, the challenging component 206 can label the generated sequence(s) 210 as −1 and the encoded amino acid sequences obtained from the first protein sequence data 212 as 1. In implementations where the challenging component 206 implements a distance function, the classification output 214 can be a number from −∞ to ∞. In at least some examples, the amino acid sequences obtained from the first protein sequence data 212 can be referred to as ground truth data.

The protein sequences included in the first protein sequence data 212 can be subject to data preprocessing 216 before being provided to the challenging component 206. In one or more implementations, the first protein sequence data 212 can be arranged according to a classification system, also referred to as a classification schema, before being provided to the challenging component 206. The data preprocessing 216 can include pairing amino acids included in the proteins of the first protein sequence data 212 with numerical values that can represent structure-based positions within the proteins. The numerical values can include a sequence of numbers having a starting point and an ending point. In an illustrative example, a T can be paired with the number 43 indicating that a Threonine molecule is located at a structure-based position 43 of a specified protein domain type. In one or more illustrative examples, structure-based numbering can be applied to any general protein type, such as fibronectin type III (FNIII) proteins, avimers, antibodies. VHH domains, kinases, zinc fingers, and the like.

In one or more implementations, the classification system implemented by the data preprocessing 216 can designate a particular number of positions for certain regions of proteins. For example, the classification system can designate that portions of proteins have particular functions and/or characteristics can have a specified number of positions. In various situations, not all of the positions included in the classification system may be associated with an amino acid because the number of amino acids in a specified region of a protein may vary between proteins. To illustrate, the number of amino acids in a region of a protein can vary for different types of proteins. In one or more examples, positions of the classification system that are not associated with a particular amino acid can indicate various structural features of a protein, such as a turn or a loop. In an illustrative example, a classification system for antibodies can indicate that heavy chain regions, light chain regions, and hinge regions have a specified number of positions assigned to them and the amino acids of the antibodies can be assigned to the positions according to the classification system.

The data used to train the generative adversarial network architecture 202 can impact the amino acid sequences produced by the generating component 204. For example, in situations where antibodies are included in the first protein sequence data 212 provided to the challenging component 206, the amino acid sequences generated by the generating component 204 can correspond to antibody amino acid sequences. In one or more additional examples, in scenarios where T-cell receptors are included in the first protein sequence data 212 provided to the challenging component 206 the amino acid sequences generated by the generating component 204 can correspond to T-cell receptor amino acid sequences. In one or more additional examples, in situations where kinases are included in the first protein sequence data 212 provided to the challenging component 206, the amino acid sequences generated by the generating component 204 can correspond to amino acid sequences of kinases. In implementations where amino acid sequences of a variety of different types of proteins are included in the first protein sequence data 212 provided to the challenging component 206, the generating component 204 can generate amino acid sequences having characteristics of proteins generally and may not correspond to a particular type of protein. Further, in various examples, the amino acid sequences produced by the generating component 204 can correspond to the types of proportions of amino acid sequences included in the first protein sequence data 212 provided to the challenging component 206.

The output produced by the data preprocessing 216 can include structured sequences 218. The structured sequences 218 can include a matrix indicating amino acids associated with various positions of a protein. In one or more examples, the structured sequences 218 can include a matrix having columns corresponding to different amino acids and rows that correspond to structure-based positions of proteins. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. The generated sequence(s) 210 can also be represented using a vector according to a same or similar number scheme as used for the structured sequences 218. In at least some illustrative examples, the structured sequences 218 and the generated sequence(s) 210 can be encoded using a method that may be referred to as a one-hot encoding method.

After the generative adversarial network architecture 202 has undergone a training process, one or more first trained generating components 220 can be generated that can produce amino acid sequences of proteins. In one or more examples, the training process for the generative adversarial network architecture 202 can be complete after the function (s) implemented by the generating component 204 and the function(s) implemented by the challenging component 206 converge. The convergence of a function can be based on the movement of values of model parameters toward specified values as protein sequences are generated by the generating component 204 and feedback is obtained from the challenging component 206. In various implementations, the training of the generative adversarial network architecture 202 can be complete when the protein sequences generated by the generating component 204 have one or more specified characteristics. To illustrate, the amino acid sequences generated by the generating component 204 can be analyzed by a software tool that can analyze amino acid sequences to determine at least one of biophysical properties of the amino acid sequences, structural features of the amino acid sequences, or adherence to amino acid sequences corresponding to one or more protein germlines.

The one or more first trained generating components 220 can undergo transfer learning at 222 based on second protein sequence data 224. The transfer learning that is performed at 222 can modify the one or more first trained generating components 220 based on the amino acid sequences included in the second protein sequence data 224. The transfer learning that is performed at 222 can be performed using one or more modified generative adversarial network architectures 226. The one or more modified generative adversarial network architectures 226 can include at least a portion of the one or more first trained generating components 220 and one or more additional challenging components. In various examples, the transfer learning that takes place at 222 can include an additional training process of the one or more first trained generating components 220 using training data obtained from the second protein sequence data 224. By using a training dataset to produce the one or more second trained generating components 228 that is different from the training dataset used to produce the one or more first trained generating components 220, the one or more modified generative adversarial network architectures 226 can produce amino acid sequences that can have some general characteristics that correspond to the amino acid sequences included in the first protein sequence data 212 and that also have one or more specified characteristics that correspond to features of the proteins related to the amino acid sequences included in the second protein sequence data 224.

In various implementations, the one or more first trained generating components 220 can be further trained using the second protein sequence data 224 as part of the transfer learning at 222 to produce one or more second trained generating components 228 in a manner that is similar to the training of the generative adversarial network architecture 202 that produced the one or more first trained generating components 220. In one or more examples, components of the one or more modified generative adversarial network architectures 226 can be trained to minimize at least one loss function. Additionally, the training process used in the transfer learning at 222 to produce the one or more second trained generating components 228 can be complete after one or more modified functions implemented by the one or more modified generative adversarial network architectures 226 converge. In one or more further examples, the training process used to generate the one or more second trained generating components 228 from the one or more first trained generating components 220 can be complete based on an analysis of a software tool indicating that amino acid sequences produced using the one or more modified generative adversarial network architectures 226 corresponds to one or more specified criteria. The one or more specified criteria can correspond to at least one of one or more structural features of proteins or one or more biophysical properties of proteins.

In one or more examples, the second protein sequence data 224 can include amino acid sequences of proteins that have features that are different from the features of the proteins related to the first protein sequence data 212. In various examples, the second protein sequence data 224 can include a subset of the amino acid sequences included in the first protein sequence data 212. In one or more additional examples, the second protein sequence data 224 can include a greater number of a group of amino acid sequences having one or more specified characteristics in relation to the number of amino acid sequences having the one or more characteristics included in the first protein sequence data 212. For example, the first protein sequence data 212 can include amino acid sequences of proteins having a variety of structural features. To illustrate, the first protein sequence data 212 can include a number of amino acid sequences of proteins having one or more sizes of hydrophobic regions, a number of amino acid sequences of proteins having one or more sizes of negatively charged regions, a number of amino acid sequences of proteins having one or more sizes of positively charged regions, a number of amino acid sequences of proteins one or more sizes of polar regions, one or more combinations thereof, and the like. In one or more implementations, the second protein sequence data 224 can include amino acid sequences of proteins that have a greater number of amino acid sequences of proteins having a subset of the properties of the proteins included in the first protein sequence data 212, such as a greater number of amino acid sequences of proteins that have hydrophobic regions with a specified range of sizes than the number of amino acid sequences included in the first protein sequence data 212 that have the hydrophobic regions with the specified range of sizes. In these scenarios, the one or more second trained generating components 228 can primarily produce amino acid sequences of proteins having hydrophobic regions with the specified range of sizes.

In one or more implementations, the amino acid sequences included in the second protein sequence data 224 can include a filtered set of amino acid sequences. For example, a set of amino acid sequences can be evaluated according to one or more criteria. In various examples, at least one of one or more software tools, one or more diagnostic tools, or one or more analytical instruments can be used to identify amino acid sequences included in the set of amino acid sequences that correspond to the one or more criteria. The amino acid sequences that satisfy the one or more criteria can then be added to the second protein sequence data 224. In one or more illustrative examples, a number of amino acid sequences can be evaluated to identify proteins having at least one polar region for inclusion in the second protein sequence data 224. In these scenarios, the amino acid sequences that include at least one polar region can be used to modify the one or more first trained generating components 220 during the transfer learning at 222 to produce the one or more second trained generating components 228 that can produce amino acid sequences of proteins having at least one polar region.

The one or more second trained generating components can generate amino acid sequences based on second input data 230. In one or more examples, the second input data 230 can include a random or pseudo-random series of numbers that can be used by the one or more second trained generating components 228 to produce amino acid sequences. In various examples, the one or more second trained generating components 228 can include multiple generating components that each generate amino acid sequences of proteins having a different distribution of values for a structural feature. For example, the second trained generating components 228 can include a first generating component that produces amino acid sequences of proteins having one or more negatively charged regions with a first range of sizes and a second generating component that produces amino acid sequences of proteins having one or more negatively charged regions with a second range of sizes. In one or more examples, there may be some overlap between the sizes of negatively charged regions included in the first range of sizes and the second range of sizes.

The amino acid sequences generated by the one or more second trained generating components 228 can include training sequences 232 that can be used to train an inferential model architecture 234. The inferential model architecture 234 can obtain input sequences 236 and the inferential model architecture 234 can determine classification data 238 for the input sequences 236. The classification data 238 can indicate one or more classifications for individual input sequences 236. The input sequences 236 can include amino acid sequences of proteins that are to be classified by the inferential model architecture 234. For example, the inferential model architecture 234 can identify amino acid sequences included in the input sequences 236 that correspond to a plurality of classifications of proteins. In one or more examples, the inferential model architecture 234 can identify amino acid sequences that correspond to proteins having one or more structural features. To illustrate, the inferential model architecture 234 can differentiate between amino acid sequences of a first group of proteins having one or more first characteristics and amino acid sequences of a second group of proteins having one or more second characteristics that are different from the one or more first characteristics.

Although not shown in the illustrative example of FIG. 2, in at least some instances, the classification data 238 can be provided to a regression model architecture that can determine one or more characteristics of proteins based on one or more classifications of the proteins indicated by the classification data 238. For example, the classification data 238 can indicate one or more structural features of one or more proteins and the regression model architecture can determine one or more biophysical properties of the one or more proteins based on the one or more structural features indicated by the classification data 238. The one or more biophysical properties can include properties that can be used to characterize a protein molecule, such as solubility, decomposition temperature (e.g., melting temperature), bioactivity, immunogenicity, viscosity, pKa, aggregation behavior, unfolding behavior, one or more combinations thereof, and the like. In various examples, the regression model architecture can also determine values related to the production of proteins corresponding to the input sequences 236, such as yield, purity, titer, and so forth.

Figure 3:
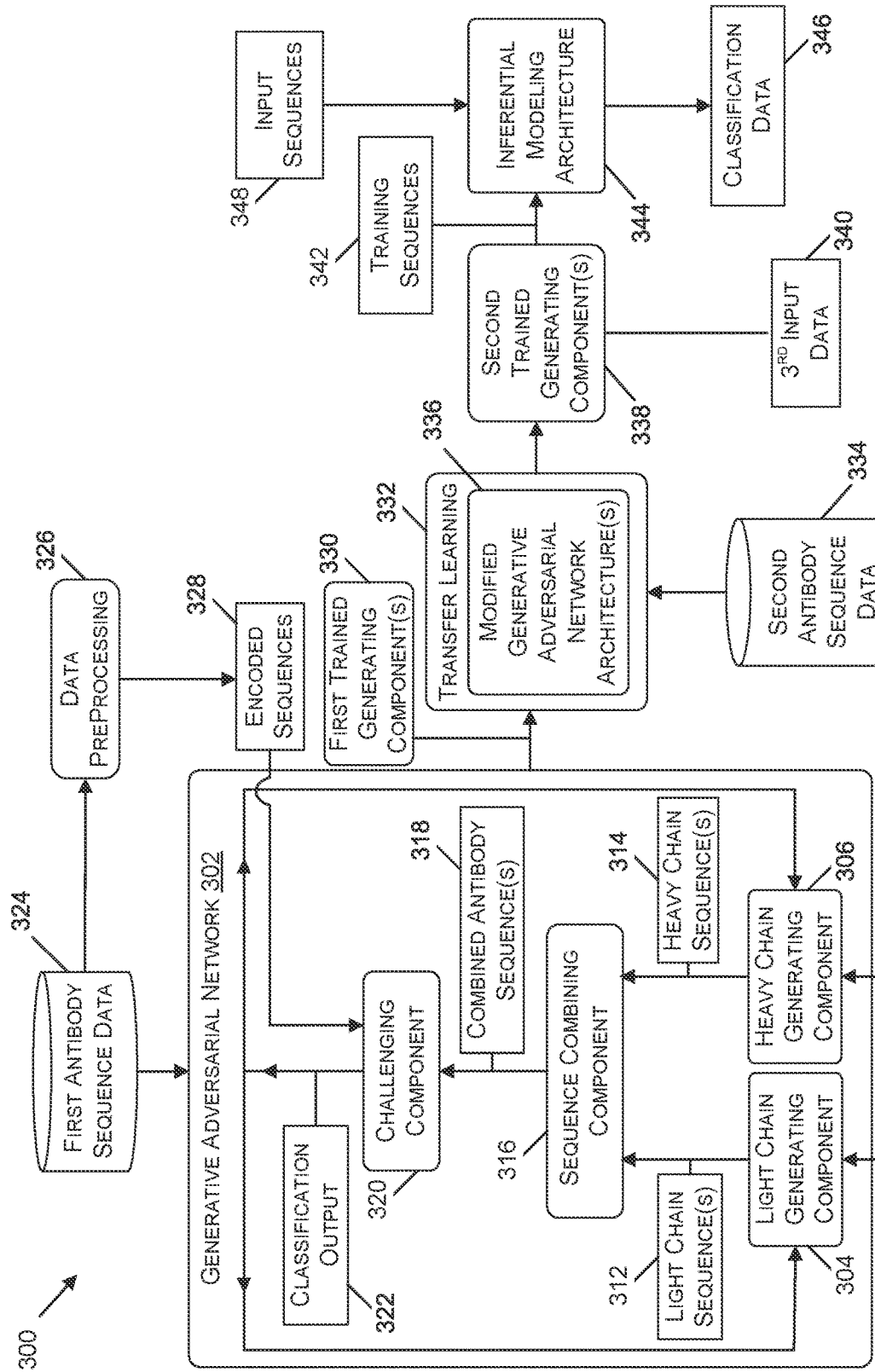
FIG. 3 is a diagram illustrating an example framework including a number of generative adversarial networks to produce antibody sequences for training an inferential model that classifies antibodies, in accordance with one or more implementations.

FIG. 3 is a diagram illustrating an example framework 300 including a number of generative adversarial networks to produce antibody sequences for training an inferential model that classifies antibodies, in accordance with one or more implementations. The framework 300 can include a generative adversarial network 302. The generative adversarial network 302 can implement one or more neural network technologies. For example, the generative adversarial network 302 can implement one or more recurrent neural networks. Additionally, the generative adversarial network 302 can implement one or more convolutional neural networks. In certain implementations, the generative adversarial network 302 can implement a combination of recurrent neural networks and convolutional neural networks.

The generative adversarial network 302 can include a light chain generating component 304 and a heavy chain generating component 306. The light chain generating component 304 can implement one or more first models to generate data corresponding to amino acid sequences of at least a portion of light chains of antibodies. In addition, the heavy chain generating component 306 can implement one or more second models to generate data corresponding to amino acid sequences of at least a portion of heavy chains of antibodies. The light chain generating component 304 can implement one or more first models to generate amino acid sequences of light chains of antibodies based on first input data 308 provided to the light chain generating component 304. The heavy chain generating component 306 can implement one or more second models to generate amino acid sequences of heavy chains of antibodies based on second input data 310. The first input data 308 can include first noise data generated by a random number generator or a pseudo-random number generator. The second input data 310 can include second noise data generated by a random number generator or a pseudo-random number generator.

The light chain generating component 304 can implement one or more first models to produce light chain sequences 312 based on the first input data 308. The one or more first models can include one or more functions having one or more variables, one or more parameters, one or more weights, or one or more combinations thereof. The light chain sequences 312 can comprise data corresponding to amino acids that are located at positions of antibody light chains. The light chain sequences 312 can include sequences of amino acids of antibody light chains that are encoded according to one or more encoding schemes. In various examples, the light chain sequences 312 can include data corresponding to amino acids at individual positions of antibody light chains that is encoded according to a schema. In one or more illustrative examples, the light chain sequences 312 can include amino acid sequences of antibody light chains that are encoded according to a one-hot encoding scheme.

The heavy chain generating component 306 can implement one or more second models to produce heavy chain sequences 314 based on the second input data 310. The one or more second models can include one or more additional functions having one or more variables, one or more parameters, one or more weights, or one or more combinations thereof. The heavy chain sequences 314 can comprise data corresponding to amino acids that are located at positions of antibody heavy chains. The heavy chain sequences 314 can include sequences of amino acids of antibody light chains that are encoded according to one or more encoding schemes. In various examples, the heavy chain sequences 314 can include data corresponding to amino acids at individual positions of antibody heavy chains that is encoded according to a schema. In one or more illustrative examples, the heavy chain sequences 314 can include amino acid sequences of antibody heavy chains that are encoded according to a one-hot encoding scheme.

The light chain sequences 312 and the heavy chain sequences 314 can be provided to a sequence combining component 316. The sequence combining component 316 can combine at least one light chain sequence 312 and at least one heavy chain sequence 314 to generate a combined antibody sequence 318. In various implementations, the sequence combining component 316 can combine a single light chain sequence 312 with a single heavy chain sequence 314. A combined antibody sequence 318 can include data corresponding to amino acids located at positions of one or more light chain sequences 312 and one or more heavy chain sequences 314.

In one or more examples, the sequence combining component 316 can generate a combined antibody sequence 318 by concatenating one or more light chain sequences 312 and one or more heavy chain sequences 314. For example, the sequence combining component 316 can add a first string of alphanumeric characters representative of an antibody light chain sequence to a second string of alphanumeric characters representative of an antibody heavy chain sequence to generate a combined antibody sequence 318. The combined antibody sequence 318 can include a first portion that corresponds to a light chain sequence 312 and a second portion that corresponds to a heavy chain sequence 314. To illustrate, a first number of positions of a combined antibody sequence 318 can correspond to amino acids of a light chain sequence 312 and a second number of positions of the combined antibody sequence 318 that are after, or subsequent to, the first number of positions can correspond to a heavy chain sequence 314. In one or more illustrative examples, the combined antibody sequences 318 generated by the sequence combining component 316 can include a string of letters representing an amino acid sequence of an antibody that is produced by adding a string of letters corresponding to an amino acid sequence included a heavy chain sequence 314 after a last letter of a string of letters corresponding to an amino acid sequence included in a light chain sequence 312. To illustrate, a light chain sequence 312 can terminate in VESG and a heavy chain sequence 314 can begin with EIQM. The sequence combining component 316 can combine the light chain sequence 312 with the heavy chain sequence 314 by adding the heavy chain sequence 314 starting with EIQM after the VESG of the light chain sequence 312. In one or more additional examples, a first number of positions of a combined antibody sequence 318 can correspond to amino acids of a heavy chain sequence 314 and a second number of positions of the combined antibody sequence 318 that are after the first number of positions can correspond to a light chain sequence 312. In various implementations, the combined antibody sequence 318 can correspond to amino acids of one or more light chain sequences 312 and one or more heavy chain sequences 314 arranged according to a schema.

In one or more scenarios, the sequence combining component 316 can include a number of computation layers. In one or more examples, the sequence combining component 316 can include one or more first computation layers to generate combined antibody sequences 318 by concatenating one or more light chain sequences 312 with one or more heavy chain sequences 314. Additionally, the sequence combining component 316 can include one or more second computation layers that modify output from the one or more first computation layers. In various examples, the one or more second computation layers can be utilized in situations where relationships between amino acid sequences and one or more biophysical properties are not accounted for by the one or more first computation layers. Additionally, the one or more second computation layers can be utilized in situations where nonlinear relationships are present between the heavy chain amino acid sequences 314 and the light chain amino acid sequences 312. Further, the one or more second computation layers can be utilized in scenarios where there are various interactions between the light chain sequences 312 and the heavy chain sequences 314 that can be captured by the one or more first computation layers.

In one or more additional implementations, the light chain generating component 304 can generate amino acid sequences of a portion of antibody light chains. For example, the light chain generating component 304 can generate amino acid sequences of at least a portion of one or more variable regions of antibody light chains. In various examples, the light chain generating component 304 can generate amino acid sequences of at least a portion of one or more antigen binding regions of antibody light chains. In one or more illustrative examples, the light chain generating component 304 can generate amino acid sequences of at least a portion of one or more complementarity determining regions (CDRs) of antibody light chains. Additionally, the light chain generating component 304 can generate amino acid sequences of one or more constant regions of antibody light chains.

The heavy chain generating component 306 can generate amino acid sequences of a portion of antibody heavy chains. To illustrate, the heavy chain generating component 306 can generate amino acid sequences of at least a portion of one or more variable regions of antibody heavy chains. In one or more examples, the heavy chain generating component 306 can generate amino acid sequences of at least a portion of one or more antigen binding regions of antibody heavy chains. Additionally, the heavy chain generating component 306 can generate amino acid sequences of at least a portion of one or more complementarity determining regions (CDRs) of antibody heavy chains. Further, the heavy chain generating component 306 can generate amino acid sequences of one or more constant regions of antibody heavy chains.

In situations where the light chain generating component 304 generates a portion of an amino acid sequence of an antibody light chain, a remainder of the amino acid sequence of the antibody light chain can be obtained from one or more sources of amino acid sequences of antibody light chains. In one or more illustrative examples, the light chain generating component 304 can generate amino acid sequences corresponding to one or more CDRs of antibody light chains and the framework regions for the antibody light chains can be obtained from one or more data sources that store amino acid sequences of antibody light chain framework regions. In one or more additional examples, a template antibody light chain can be obtained that indicates one or more regions that are to be generated by the light chain generating component 304. For example, a template antibody sequence can include an amino acid sequence of an antibody light chain that is missing a CDR3. In these scenarios, the light chain generating component 304 can generate amino acid sequences of CDR3s that can be used in conjunction with the template antibody sequence to produce amino acid sequences of antibody light chains. In further examples, in implementations where a template antibody sequence includes amino acid sequences of constant regions of antibody light chains, the light chain generating component 304 can generate amino acid sequences of variable regions of antibody light chains that can be used in conjunction with the template antibody sequence to produce amino acid sequences of antibody light chains. In implementations where the light chain generating component 304 generates a portion of an amino acid sequence of antibody light chains, the output from the light chain generating component 304 can be combined with additional amino acid sequences of missing regions of the antibody light chains to produce the light chain sequences 312. In this way, the light chain sequences 312 can be assembled using amino acid sequences produced by the light chain generating component 304 and additional amino acid sequences obtained from one or more additional data sources that fill in portions of antibody light chains that are absent from the amino acid sequences produced by the light chain generating component 304.

In addition, in instances where the heavy chain generating component 306 generates a portion of an amino acid sequence of an antibody heavy chain, a remainder of the amino acid sequence of the antibody heavy chain can be obtained from one or more sources of amino acid sequences of antibody heavy chains. For example, the heavy chain generating component 306 can generate amino acid sequences corresponding to one or more CDRs of antibody heavy chains and the framework regions for the antibody heavy chains can be obtained from one or more data sources that store amino acid sequences of antibody heavy chain framework regions. In one or more additional examples, a template antibody heavy chain can be obtained that indicates one or more regions that are to be generated by the heavy chain generating component 306. To illustrate, a template antibody sequence can include an amino acid sequence of an antibody heavy chain that is missing a CDR3. In these scenarios, the heavy chain generating component 306 can generate amino acid sequences of CDR3s that can be used in conjunction with the template antibody sequence to produce amino acid sequences of antibody heavy chains. In one or more examples, in implementations where a template antibody sequence includes amino acid sequences of constant regions of antibody heavy chains, the heavy chain generating component 306 can generate amino acid sequences of variable regions of antibody heavy chains that can be used in conjunction with the template antibody sequence to produce amino acid sequences of antibody heavy chains. In implementations where the heavy chain generating component 306 generates a portion of an amino acid sequence of antibody heavy chains, the output from the heavy chain generating component 306 can be combined with additional amino acid sequences to produce the heavy chain sequences 314. In this way, the heavy chain sequences 314 can be assembled using amino acid sequences produced by the heavy chain generating component 306 and additional amino acid sequences obtained from one or more additional data sources that fill in portions of antibody heavy chains that are absent from the amino acid sequences produced by the heavy chain generating component 306.

The generative adversarial network 302 can include a challenging component 320. The challenging component 320 can generate output indicating that the combined antibody sequences 318 satisfy or do not satisfy one or more criteria. The challenging component 320 can produce classification output 322 that can be provided to the light chain generating component 304 and the heavy chain generating component 306. The challenging component 320 can evaluate the combined antibody sequences 318 with respect to training data that comprises the first antibody sequence data 324. The first antibody sequence data 324 can correspond to amino acid sequences of a number of antibodies. For a given antibody, the first antibody sequence data 324 can include a pairing of an antibody light chain and an antibody heavy chain. In one or more illustrative examples, the first antibody sequence data 324 can include amino acid sequences of antibodies produced by one or more mammals. The first antibody sequence data 324 can also include amino acid sequences of one or more isotypes of classes of antibodies, such as IgA antibodies, IgD antibodies, IgE antibodies, IgG antibodies, and/or IgM antibodies.

The challenging component 320 can compare the combined antibody sequences 318 generated by the sequence combining component 316 with at least a portion of the amino acid sequences included in the first antibody sequence data 324. The classification output 322 generated based on the comparisons can indicate an amount of correspondence between a combined antibody sequence 318 with respect to at least a portion of the amino acid sequences included in the first antibody sequence data 324. For example, based on similarities and/or differences between a combined antibody sequence 318 and at least a portion of the amino acid sequences included in the first antibody sequence data 324, the classification output 322 generated by the challenging component 320 can indicate an amount of similarity and/or an amount of difference between the combined antibody sequence 318 and at least a portion of the amino acid sequences included in the first antibody sequence data 324. The classification output 322 can be based on a type of architecture associated with the generative adversarial network 302. For example, for a first type of generative adversarial network, the challenging component 320 can generate a classification output 322 of 1 for a combined antibody sequence 318 that has at least a threshold amount of correspondence with respect to amino acid sequences included in training data provided to the challenging component 320. Also, for the first type of generative adversarial network, the challenging component 320 can generate a classification output of 0 for a combined antibody sequence 318 that has less than a threshold amount of correspondence with respect to amino acid sequences included in training data provided to the challenging component 320. In various examples, for the first type of generative adversarial network, the challenging component 320 can generate classification output 322 that labels a combined antibody sequence 318 using a numerical scale from 0 to 1 based on an amount of similarity between the combined antibody sequence 318 and amino acid sequences included in training data provided to the challenging component 320.

Additionally, in situations where the generative adversarial network 302 implements a second type of architecture, such as a Wasserstein GAN, the challenging component 320 can execute a distance function that produces a classification output 322 that indicates an amount of distance between the combined antibody sequences 318 and amino acid sequences included in training data provided to the challenging component 320. For example, the challenging component 320 can produce a classification output 322 that includes a number from $-\infty$ to $\infty$ that indicates a distance between a combined antibody sequence 318 and at least a portion of the amino acid sequences included in the first antibody sequence data 324. In various examples, the training data obtained from the first antibody sequence data 324 can be referred to as ground truth data.

The amino acid sequences included in the first antibody sequence data 324 can be subject to data preprocessing 326 before being provided to the challenging component 320. In one or more implementations, the data preprocessing 326 can include arranging the first antibody sequence data 324 according to a classification system before being provided to the challenging component 320. For example, the data preprocessing 326 can include pairing amino acids included in the amino acid sequences of the first antibody sequence data 324 with numerical values that can represent structure-based positions within the antibodies. The numerical values can include a sequence of numbers having a starting point and an ending point. The first antibody sequence data 324 can separately store amino acid sequences of antibody light chains and amino acid sequences of antibody heavy chains. Further, the first antibody sequence data 324 can store amino acid sequences of combinations of antibody light chains and antibody heavy chains.

The output produced by the data preprocessing 326 can include structured sequences 328. The structured sequences 328 can include a matrix indicating amino acids associated with various positions of an antibody. In one or more examples, the structured sequences 328 can include a matrix having columns corresponding to different amino acids and rows that correspond to structure-based positions of antibodies. For each element in the matrix, a 0 can be used to indicate the absence of an amino acid at the corresponding position and a 1 can be used to indicate the presence of an amino acid at the corresponding position. In situations where a position represents a gap in an amino acid sequence, the row associated with the position can comprise zeroes for each column. In at least some illustrative examples, the structured sequences 328 and the combined antibody sequence(s) 318 can be encoded using a method that may be referred to as a one-bot encoding method. In various implementations, the structured sequences 328 can include an amino acid sequence of an antibody light chain followed by an amino acid sequence of an antibody heavy chain. In one or more additional implementations, the structured sequences 328 can include an amino acid sequence of an antibody heavy chain followed by an amino acid sequence of an antibody light chain. The arrangement of antibody light chains and antibody heavy chains in the structured sequences 328 can correspond to the arrangement of antibody light chains and antibody heavy chains included in the combined antibody sequences 318.

In various examples, training of the light chain generating component 304 and the heavy chain generating component 306 can take place asynchronously. For example, the training of the heavy chain component 306 may cease for a period of time while training of the light chain generating component 304 continues. In one or more examples, the light chain generating component 304 and the heavy chain generating component 306 can train concurrently for a period of time. During this period of time, the training of the heavy chain generating component 306 may progress faster than training of the light chain generating component 304. In these situations, the training of the heavy chain generating component 306 may cease for a period of time that the light chain generating component 304 continues to train. In at least some examples, sequences generated by the heavy chain generating component 306 may be evaluated at various points in time to determine a metric with regard to quality of the amino acid sequences generated by the heavy chain generating component 306. In various examples, the training of the heavy chain generating component 306 may cease when the metric satisfies one or more threshold metrics. The light chain generating component 304 may continue to train until the sequences produced by the light chain generating component 304 satisfy the one or more threshold metrics. After sequences from both the light chain generating component 304 and the heavy chain generating component 306 satisfy the one or more threshold metrics, the light chain generating component 304 and the heavy chain generating component 306 can continue to train. In one or more examples, training of the light chain generating component 304 and the heavy chain generating component 306 can train until one or more metrics used to evaluate the sequences produced by the light chain generating component 304 and the heavy chain generating component 306 diverge by at least a threshold amount.

In one or more illustrative examples, the training of the heavy chain generating component 306 can implement hobbled weights such that the training of the light chain generating component 304 and the training of the heavy chain generating component 306 proceed at relatively similar rates. Additionally, the training of the heavy chain generating component 306 may proceed with slower gradients such that the training of the light chain generating component 304 and the training of the heavy chain generating component 306 proceed at relatively similar rates.

After the generative adversarial network 302 has undergone a training process, one or more first trained generating components 330 can be generated that can produce amino acid sequences of antibodies. The one or more first trained generating components 330 can include at least one of the light chain generating component 304 or the heavy chain generating component 306 after a training process using the first antibody sequence data 324. In one or more examples, the training process for the generative adversarial network 302 can be complete after the classification output 322 indicates at least a threshold amount of correspondence between the combined antibody sequences 318 and the amino acid sequences included in at least a portion of the first antibody sequence data 324. In one or more additional implementations, the training of the generative adversarial network 302 can be complete when the combined antibody sequences 318 have one or more specified characteristics. To illustrate, the amino acid sequences generated by the sequence combining component 316 can be analyzed by a software tool that can analyze amino acid sequences to determine at least one of biophysical properties of the amino acid sequences, structural features of the amino acid sequences, or adherence to amino acid sequences corresponding to one or more protein germlines. The characteristics of the combined antibody sequences 318 determined by the analysis of the software tool in relation to specified characteristics can be used to determine whether or not the training of the generative adversarial network 302 is complete.

The one or more first trained generating components 330 can undergo transfer learning at 332 based on second antibody sequence data 334. The transfer learning that is performed at 332 can modify the one or more first trained generating components 330 based on the amino acid sequences included in the second antibody sequence data 334. The transfer learning that is performed at 332 can be performed using one or more modified generative adversarial network architectures 336. The one or more modified generative adversarial network architectures 336 can include at least a portion of the one or more first trained generating components 330 and one or more additional challenging components. In one or more illustrative examples, the one or more modified generative adversarial network architectures 336 can include the light chain generating component 304 after undergoing a training process using the first antibody sequence data 324 and the heavy chain generating component 304 after undergoing a training process using the first antibody sequence data 324.

In various examples, the transfer learning that takes place at 332 can comprise a training process that is in addition to the training of the generative adversarial network 302. By using a training dataset to produce the one or more second trained generating components 338 that is different from the training dataset used to produce the one or more first trained generating components 330, the one or more second trained generating components 338 can produce amino acid sequences that can have some general characteristics that correspond to the amino acid sequences included in the first antibody sequence data 324 and that also have one or more specified characteristics that correspond to features of the proteins related to the amino acid sequences included in the second antibody sequence data 334.

In various implementations, the one or more first trained generating components 330 can be further trained using the second antibody sequence data 334 as part of the transfer learning at 332 to produce the one or more second trained generating components 338 in a manner that is similar to the training of the generative adversarial network 302 that produced the one or more first trained generating components 330. In one or more examples, components of the one or more modified generative adversarial network architectures 336 can be trained to minimize at least one loss function. Additionally, the training process used in the transfer learning at 332 to produce the one or more second trained generating components 338 can be complete after one or more modified functions implemented by the one or more modified generative adversarial network architectures 336 converge. In one or more further examples, the training process used to generate the one or more second trained generating components 338 from the one or more first trained generating components 330 can be complete based on an analysis of a software tool indicating that amino acid sequences produced using the one or more modified generative adversarial network architectures 336 correspond to one or more specified criteria. The one or more specified criteria can correspond to at least one of one or more structural features of proteins or one or more biophysical properties of proteins. In one or more implementations, the training process used to generate the one or more second trained generating components 338 can evaluate sequences produced by the one or more modified generative adversarial network architectures 336 based on at least one of agreement with amino acid sequences produced in relation to one or more germline genes, a measure of immunogenicity of the amino acid sequences, or agreement with CDR H3 amino acid sequences. A principal component analysis (PCA) model may be used to determine when to stop training the one or more modified generative adversarial network architectures 336. In various examples, the measure of immunogenicity can correspond to major histocompatibility complex (MHC) Class II binding affinity.

In one or more examples, the second antibody sequence data 334 can include amino acid sequences of proteins that have features that are different from the features of the proteins related to the first antibody sequence data 324. In various examples, the second antibody sequence data 334 can include a subset of the amino acid sequences included in the first antibody sequence data 324. In one or more additional examples, the second antibody sequence data 334 can include a greater number of a group of amino acid sequences having one or more specified characteristics in relation to the number of amino acid sequences having the one or more specified characteristics included in the first antibody sequence data 324. For example, the first antibody sequence data 324 can include amino acid sequences of proteins having a variety of structural features. To illustrate, the first antibody sequence data 324 can include a number of amino acid sequences of antibodies having various sizes of hydrophobic regions, a number of amino acid sequences of proteins having various sizes of negatively charged regions, a number of amino acid sequences of proteins having various sizes of positively charged regions, a number of amino acid sequences of proteins various sizes of polar regions, one or more combinations thereof, and the like. In one or more implementations, the second antibody sequence data 334 can include amino acid sequences of proteins that have a greater number of amino acid sequences of proteins having a subset of the properties of the proteins included in the first antibody sequence data 324, such as a greater number of amino acid sequences of proteins that have hydrophobic regions with a specified range of sizes than the number of amino acid sequences included in the first antibody sequence data 324 that have the hydrophobic regions with the specified range of sizes. In these scenarios, the one or more second trained generating components 338 can primarily produce amino acid sequences of proteins having hydrophobic regions with the specified range of sizes. In one or more instances, the second antibody sequence data 334 can separately store amino acid sequences of antibody light chains and antibody heavy chains. In additional scenarios, the second antibody sequence data 334 can store amino acid sequences of combined antibody light chains and antibody heavy chains.

In one or more implementations, the amino acid sequences included in the second antibody sequence data 334 can include a filtered set of amino acid sequences. For example, a set of amino acid sequences can be evaluated according to one or more criteria. In various examples, at least one of one or more software tools, one or more diagnostic tools, or one or more analytical instruments can be used to identify amino acid sequences included in the set of amino acid sequences that correspond to the one or more criteria. The amino acid sequences that satisfy the one or more criteria can then be added to the second antibody sequence data 334. In one or more illustrative examples, a number of amino acid sequences can be evaluated to identify antibodies having at least one negatively charged region for inclusion in the second antibody sequence data 334 that can be used to modify the one or more first trained generating components 330 during the transfer learning at 332 to produce the one or more second trained generating components 338. In one or more additional illustrative examples, the amino acid sequences included in the second antibody sequence data 334 can correspond to antibodies having a threshold level of expression in humans or a threshold amount of binding affinity to one or more molecules, such as MHC class II molecules. By using amino acid sequences in the transfer learning at 332 that have one or more specified characteristics, the one or more modified generative adversarial network architectures 336 can be trained to produce amino acid sequences of antibodies that have at least a threshold probability of having the one or more specified characteristics.

The one or more second trained generating components can generate amino acid sequences based on third input data 340. In one or more examples, the third input data 340 can include a random or pseudo-random series of numbers that can be used by the one or more second trained generating components 338 to produce amino acid sequences. In various examples, the one or more second trained generating components 338 can include multiple generating components that each generate amino acid sequences of antibodies having a different distribution of values for a structural feature or a biophysical property. For example, the second trained generating components 338 can include a first generating component that produces amino acid sequences of antibody light chains having one or more negatively charged regions with a first range of sizes and a second generating component that produces amino acid sequences of antibody light chains having one or more negatively charged regions with a second range of sizes. In one or more examples, there may be some overlap between the sizes of negatively charged regions included in the first range of sizes and the second range of sizes.

The amino acid sequences generated by the one or more second trained generating components 338 can include training sequences 342 that can be used to train an inferential model architecture 344. In one or more examples, the training sequences can include at least one light chain and at least one heavy chain that correspond to individual antibodies. In one or more additional examples, the training sequences 342 can include at least one of one or more antibody light chains or one or more antibody heavy chains.

The inferential model architecture 344 can determine classification data 346 for the input sequences 348 that indicates one or more classifications for individual input sequences 348. The input sequences 348 can include amino acid sequences of antibodies that are to be classified by the inferential model architecture 344. In various examples, the input sequences 348 can include at least one of amino acid sequences of antibody light chains, amino acid sequences of antibody heavy chains, or amino acid sequences of combinations of antibody light chains and antibody heavy chains. For example, the inferential model architecture 344 can identify amino acid sequences included in the input sequences 348 that correspond to a plurality of classifications of antibodies. In one or more examples, the inferential model architecture 344 can differentiate between amino acid sequences of a first group of antibodies having one or more first characteristics and amino acid sequences of a second group of antibodies having one or more second characteristics that are different from the one or more first characteristics.

Although not shown in the illustrative example of FIG. 3, in at least some instances, the classification data 346 can be provided to a regression model architecture that can determine one or more characteristics of antibodies based on one or more classifications of the antibodies indicated by the classification data 346. For example, the classification data 346 can indicate one or more structural features of one or more antibodies and the regression model architecture can determine one or more biophysical properties of the one or more antibodies based on the one or more structural features indicated by the classification data 346. The one or more biophysical properties can include solubility, decomposition temperature (e.g., melting temperature), bioactivity, immunogenicity, viscosity, pKa, aggregation behavior, unfolding behavior, one or more combinations thereof, and the like. In various examples, the regression model architecture can also determine values related to the production of antibodies corresponding to the input sequences 348, such as yield, purity, titer, and so forth, based on classifications of the input sequences indicating one or more biophysical properties and/or one or more structural features of proteins corresponding to the input sequences 348.

Figure 4:
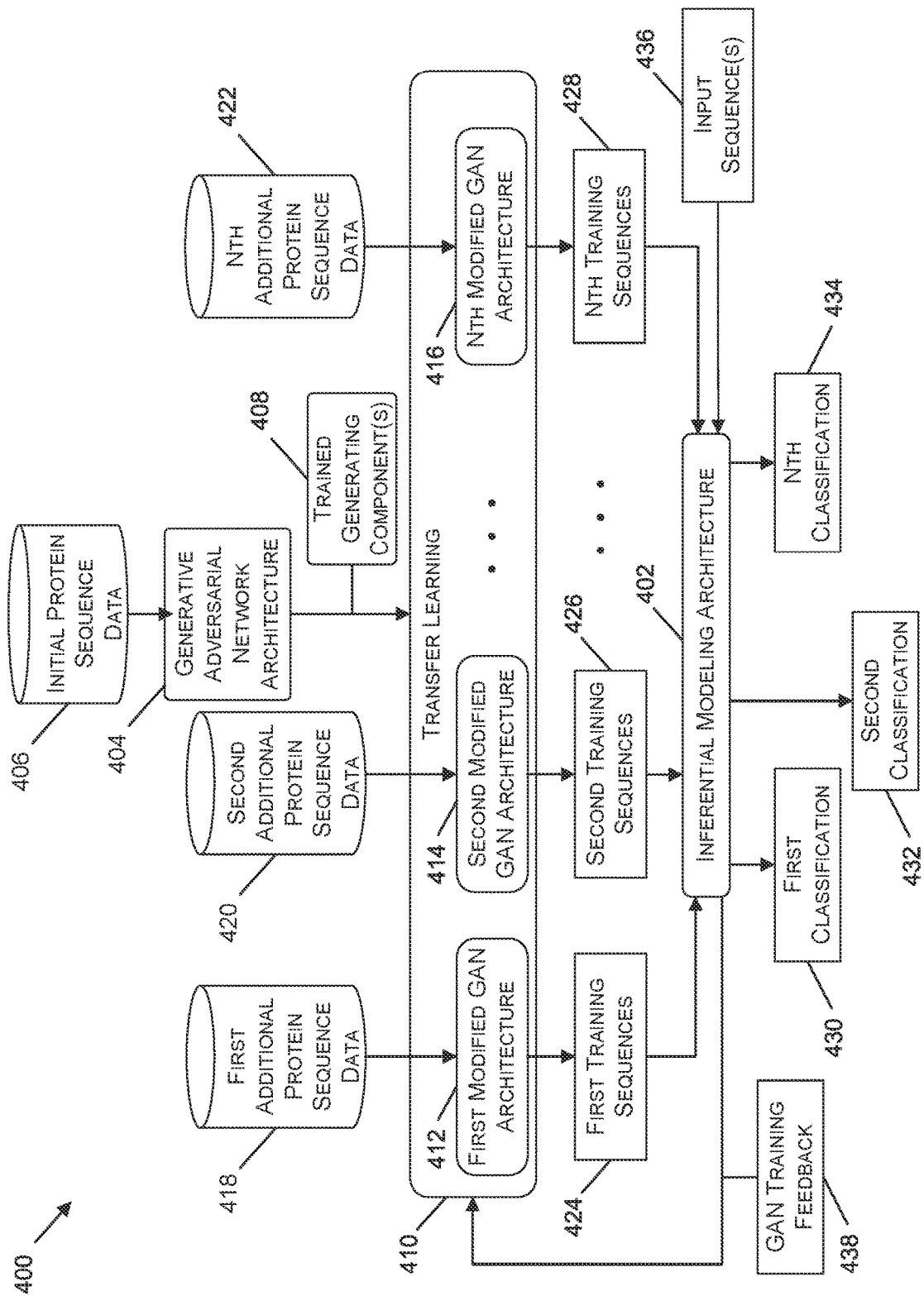
FIG. 4 is a diagram illustrating an example framework to generate an inferential model architecture based on amino acid sequences produced by a number of generative adversarial networks, in accordance with one or more implementations.

FIG. 4 is a diagram illustrating an example framework 400 to generate an inferential modeling architecture 402 based on amino acid sequences produced by a number of generative adversarial networks, in accordance with some implementations. The framework 400 can include a generative adversarial network architecture 404 that can be trained using initial protein sequence data 406. The generative adversarial network architecture 404 can include one or more generating components and one or more challenging components. During the training process, the one or more generating components of the generative adversarial network architecture 404 can produce amino acid sequences of proteins that are evaluated by the one or more challenging components of the generative adversarial network architecture 404 with respect to the initial protein sequence data 406. The initial protein sequence data 406 can be training data for the generative adversarial network architecture 404. The training process performed with respect to the generative adversarial network architecture 404 can produce one or more trained generating components 408. In one or more illustrative examples, the one or more trained generating components 408 can produce amino acid sequences of antibodies. In these scenarios, the one or more trained generating components 408 can, in one or more implementations, include at least one light chain generating component and at least one heavy chain generating component.

The one or more trained generating components 408 can be used as part of transfer learning 410. The transfer learning 410 can include additional training of the one or more trained generating components 408 using training datasets that are different from the initial protein sequence data 406. By training additional generative adversarial network architectures that include the one or more trained generating components 408 with different datasets, the additional generative adversarial networks can generate amino acid sequences of proteins that can have one or more specified characteristics. In the illustrative example of FIG. 4, the transfer learning 410 can take place with respect to a first modified generative adversarial network (GAN) architecture 412, a second modified GAN architecture 414, up to an Nth modified GAN architecture 416. The first modified GAN architecture 412, the second modified GAN architecture, up to the Nth modified GAN architecture 416 can individually include one or more challenging components and one or more generating components with the one or more generating components for each modified GAN architecture 412, 414, up to 416 being based on the one or more trained generating components 408.

The first modified CAN architecture 412 can be trained as part of the transfer learning 410 using first additional protein sequence data 418. In addition, the second modified GAN architecture 414 can be trained as part of the transfer learning 410 using second additional protein sequence data 420. Further, the Nth modified GAN architecture 416 can be trained as part of the transfer learning 410 using Nth additional protein sequence data 422. The proteins having amino acid sequences included in each of the first additional protein sequence data 418, the second additional protein sequence data 420, and the Nth additional protein sequence data 422 can have characteristics that are different from one another. For example, the proteins having amino acid sequences included in the first additional protein sequence data 418 can have at least one of structural features or biophysical properties that are different from the proteins having amino acid sequences included in the second additional protein sequence data 420 and the Nth additional protein sequence data 422. The proteins having amino acid sequences included in the second additional protein sequence data 420 can also be different from proteins having amino acid sequences included in the Nth additional protein sequence data 422.

In one or more examples, the first additional protein sequence data 418 can include amino acid sequences of proteins having at least one of a first structural feature or a first biophysical property, the second additional protein sequence data 420 can include amino acid sequences of proteins having at least of a second structural feature or a second biophysical property, and the Nth additional protein sequence data 422 can include amino acid sequences of proteins having at least a third structural feature or a third biophysical property. For example, the first additional protein sequence data 418 can include amino acid sequences of proteins having one or more hydrophobic regions, the second additional protein sequence data 420 can include amino acid sequences of proteins having one or more positively charged regions, and the Nth additional protein sequence data 422 can include amino acid sequences of proteins having one or more polar regions. In one or more additional examples, the first additional protein sequence data 418 can include amino acid sequences of proteins having at least a threshold probability of binding to one or more specified antigens, the second additional protein sequence data 420 can include amino acid sequences of proteins having at least a threshold melting temperature, and the Nth additional protein sequence data 422 can include amino acid sequences of proteins having at least a threshold percentage of being a high molecular weight (HMW) protein. In various examples, an HMW protein can have a molecular weight that is at least 100 kilodaltons (kDa), at least 150 kDa, at least 200 kDa, or at least 250 kDa. In this way, the first modified GAN architecture 412 can produce at least a threshold amount of amino acid sequences of proteins having at least one of a first biophysical property or a first structural feature, the second modified GAN architecture 414 can produce at least a threshold amount of amino acid sequences of proteins having at least one of a second biophysical property or a second structural feature, and the Nth modified GAN architecture 416 can produce at least a threshold amount of amino acid sequences of proteins having at least one of a third biophysical property or a third structural feature.

In one or more additional implementations, the first additional protein sequence data 418, the second additional protein sequence data 420, and the Nth additional protein sequence data 422 can include amino acid sequences of proteins having at least one of a same biophysical property or a same structural feature, while having different distributions for values for the same biophysical property and/or the same structural feature. For example, the first additional protein sequence data 418 can include amino acid sequences of proteins including at least one negatively charged region having a first range of sizes, the second additional protein sequence data 420 can include amino acid sequences of proteins including at least one negatively charged region having a second range of sizes, and the Nth additional protein sequence data 422 can include amino acid sequences of proteins including at least one negatively charged region having a third range of sizes. The first range of sizes can be different from the second range of sizes and the third range of sizes and the second range of sizes can be different from the third range of sizes. In one or more examples, there can be an amount of overlap between the first range of sizes and the second range of sizes. In one or more additional examples, there can be an amount of overlap between the second range of sizes and the third range of sizes. In these scenarios, the first modified GAN architecture 412 can produce at least a threshold amount of amino acid sequences of proteins including at least one negatively charged region having the first range of sizes, the second modified GAN architecture 414 can produce at least a threshold amount of amino acid sequences of proteins including at least one negatively charged region having the second range of sizes, and the Nth modified GAN architecture 416 can produce at least a threshold amount of amino acid sequences of proteins including at least one negatively charged region having the third range of sizes.

The first modified GAN architecture 412 can produce a number of first training sequences 424 for the inferential modeling architecture 402. Additionally, the second modified GAN architecture 414 can produce a number of second training sequences 426 and the Nth modified GAN architecture 416 can produce a number of Nth training sequences 428 for the inferential modeling architecture 402. The training sequences 424, 426, 428 can be used to train the inferential modeling architecture 402 to classify amino acid sequences of proteins having different biophysical properties and/or different structural features. Additionally, the training sequences 424, 426, 428 can be used to train the inferential modeling architecture 402 to classify amino acid sequences of proteins having values of one or more structural features and/or values of one or more biophysical properties that are included in different ranges. In various examples, the inferential modeling architecture 402 can classify amino acid sequences of proteins according to a first classification 430, a second classification 432, up to an Nth classification 434. The first classification 430 can correspond to one or more features of amino acid sequences included in the first training sequences 424, the second classification 432 can correspond to one or more features of amino acid sequences included in the second training sequences 426, and the Nth classification 434 can correspond to one or more features of amino acid sequences included in the Nth training sequences 428.

In one or more examples, based on the first training sequences 424, the second training sequences 426, and the Nth training sequences 428, the inferential modeling architecture 402 can be trained to identify amino acid sequences of proteins that have a first biophysical property and/or a first structural feature, amino acid sequences of proteins that have a second biophysical property and/or a second structural feature, and amino acid sequences of proteins that have a third biophysical property and/or a third structural feature. To illustrate, the inferential modeling architecture 402 can be trained to identify first amino acid sequences of first proteins having at least a threshold melting temperature, second amino acid sequences of second proteins having at least a threshold viscosity, and third amino acid sequences of third proteins have at least a threshold measure of solubility in water. In one or more additional illustrative examples, the inferential modeling architecture 402 can be trained to identify first amino acid sequences of first proteins having one or more hydrophobic regions, second amino acid sequences of second proteins having one or more positively charged regions, and third amino acid sequences of third proteins having one or more regions having a pH that is less than 7. In one or more further illustrative examples, the inferential modeling architecture 402 can be trained to identify first amino acid sequences of first proteins having one or more polar regions that include a first number of amino acids (e.g., 1 to 4 amino acids), second amino acid sequences of second proteins having one or more polar regions that include a second number of amino acids (e.g. 5 to 8 amino acids), and third amino acid sequences of third proteins having one or more polar regions that include a third number of amino acids (e.g., 9 to 13 amino acids). Still further, the inferential modeling architecture 402 can be trained to identify first amino acid sequences of first proteins having a first range of measures of aggregation, second amino acid sequences of second proteins having a second range of measures of aggregation, and third amino acid sequences of third proteins having a third range of measures of aggregation.

In various implementations, the inferential modeling architecture 402 can determine a probability of amino acid sequences corresponding to one or more classifications. To illustrate, one or more input sequences 436 can be provided to the inferential modeling architecture 402. The inferential modeling architecture 402 can then determine one or more probabilities that the one or more input sequences 436 correspond to one or more classifications. For example, the inferential modeling architecture 402 can determine a first probability that an input sequence 436 corresponds to the first classification 430, a second probability that the input sequence 436 corresponds to the second classification 432, and a third probability that the input sequence 436 corresponds to the Nth classification 434. The inferential modeling architecture 402 can determine a classification corresponding to the input sequence 436 by analyzing the first probability, the second probability, and the third probability with respect to a threshold probability. In situations where the first probability, the second probability, or the third probability correspond to the threshold probability, the inferential modeling architecture 402 can determine that the classification having the respective probability corresponding to the threshold probability is identified as the classification for the input sequence 436. For example, the inferential modeling architecture 402 can determine that a probability associated with the input sequence 436 with respect to the second classification 432 satisfies the threshold probability. In these scenarios, the inferential modeling architecture 402 can classify the input sequence 436 according to the second classification 432.

In one or more scenarios, the inferential modeling architecture 402 can produce GAN training feedback 438 that can be used in the transfer learning 410. In one or more examples, the GAN training feedback 438 can indicate one or more amino acid sequences that the inferential modeling architecture 402 determined to have less than a threshold probability of corresponding to at least one of the first classification 430, the second classification 432, up to the Nth classification 434. In various examples, the one or more amino acid sequences that have less than a threshold probability of corresponding to at least one of the first classification 430, the second classification 432, up to the Nth classification 434 can be associated with an inconclusive classification. That is, the one or more amino acid sequences may have been difficult for the inferential modeling architecture 402 to classify. In various examples, the inferential modeling architecture 402 can be trained iteratively based on the GAN training feedback 438.

The GAN training feedback 438 can be used in the transfer learning 410 to train at least one of the first modified GAN architecture 412, the second modified GAN architecture 414, up to the Nth modified GAN architecture 416. For example, the training of at least one of the first modified GAN architecture 412, the second modified GAN architecture 414, up to the Nth modified GAN architecture 416 can be impacted by the GAN training feedback 438 with respect to the modification of at least one of one or more parameters, one or more weights, or one or more functions of the first modified GAN architecture 412, the second modified GAN architecture 414, and/or up to the Nth modified CAN architecture 416. In one or more additional examples, the GAN training feedback 438 can modify the training sequences provided to the inferential modeling architecture 402 by at least one of the first modified GAN architecture 412, the second modified GAN architecture 414, or up to the Nth modified GAN architecture 416. To illustrate, in situations where the GAN training feedback 438 indicates one or more amino acid sequences that do not satisfy one or more criteria for at least one classification of the inferential modeling architecture 402, at least one of the first training sequences 424, the second training sequences 426, or up to the Nth training sequences 428 can be modified such that amino acid sequences having at least a threshold amount of identity with the one or more sequences included in the GAN training feedback 438 are not included in the first training sequences 424, the second training sequences 426, and/or up to the Nth training sequences 428. In one or more illustrative examples, the GAN training feedback 438 can indicate an amino acid sequence that does not satisfy one or more criteria for at least one classification of the inferential modeling architecture 402. In these instances, the transfer learning 410 can include monitoring the amino acid sequences produced by the first modified GAN architecture 412, the second modified GAN architecture 414, and/or up to the Nth modified GAN architecture 416 for amino acid sequences that have at least a threshold amount of identity with the amino acid sequence included in the GAN training feedback 438. In scenarios where a respective amino acid sequence produced by at least one of the first modified GAN architecture 412, the second modified GAN architecture 414, or up to the Nth modified GAN architecture 416, has at least at threshold amount of identity with the amino acid sequence included in the GAN training feedback, the respective amino acid sequence can be excluded from at least one of the first training sequences 424, the second training sequences 426, or up to the Nth training sequences 428. In this way, the efficiency and accuracy of the inferential modeling architecture 402 can be increased due to the training of the inferential modeling architecture 402 being based on amino acid sequences that are more readily classified by the inferential modeling architecture 402.

Figure 5:
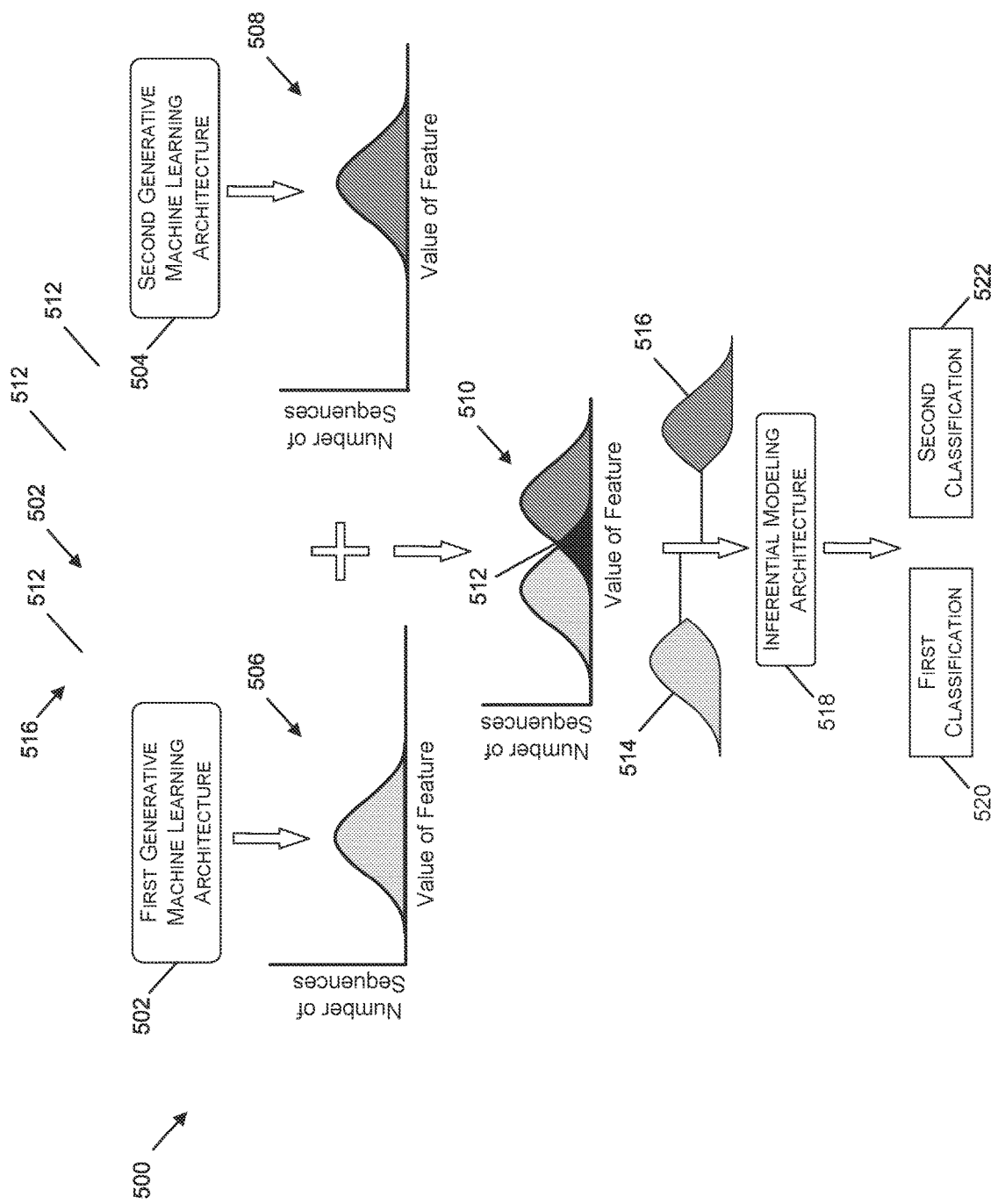
FIG. 5 is a diagram illustrating an example framework to determine amino acid sequences having a range of values for a feature of a protein that are used to train an inferential model, in accordance with one or more implementations.

FIG. 5 is a diagram illustrating an example framework to determine amino acid sequences having a range of values for a feature of a protein that are used to train an inferential model, in accordance with some implementations. The framework 500 can include a first generative machine learning architecture 502 and a second generative machine learning architecture 504. The first generative machine learning architecture 502 and the second generative machine learning architecture 504 can individually include one or more generative adversarial networks. In one or more additional examples, the first generative machine learning architecture 502 and the second generative machine learning architecture 504 can individually include one or more autoencoders.

The first generative machine learning architecture 502 can generate first amino acid sequences of proteins having a first distribution 506 that corresponds to a first range of values for a feature of the proteins. The second generative machine learning architecture 504 can generate amino acid sequences of proteins having a second distribution 508 that corresponds to a second range of values for the feature of the proteins. The feature of the proteins can include a biophysical property or a structural feature. In one or more examples, the first generative machine learning architecture 502 and the second generative machine learning architecture 504 can undergo at least a portion of one or more training processes to produce the first amino acid sequences that correspond to the first distribution 506 and the second amino acid sequences that correspond to the second distribution 508. In the illustrative example of FIG. 5, a combined distribution 510 of the first distribution 506 and the second distribution 508 can include an overlap region 512. The overlap region 512 can indicate values for the feature where amino acid sequences produced by the first generative machine learning architecture 502 and amino acid sequences produced by the second generative machine learning architecture 504 have the same or similar values.

In one or more implementations, a first modified distribution 514 can be determined that includes a portion of the first distribution 506 that does not include amino acid sequences having values for the feature that are included in the overlap region 512. In addition, a second modified distribution 516 can be determined that includes a portion of the second distribution that does not include amino acid sequences having values for the feature that are included in the overlap region 512. The amino acid sequences that correspond to the first modified distribution 514 and the amino acid sequences that correspond to the second modified distribution 516 can be provided to an inferential modeling architecture 518 to train the inferential modeling architecture 518 to classify amino acid sequences of proteins. In the illustrative example of FIG. 5, the inferential modeling architecture 518 can be trained to classify amino acids according to a first classification 520 and a second classification 522. The first classification 520 can correspond to a feature of amino acid sequences related to the first modified distribution 514 and the second classification 522 can correspond to an additional feature of amino acid sequences related to the second modified distribution 516. By training the inferential modeling architecture 518 using the first modified distribution 514 and the second modified distribution 516 without the amino acid sequences corresponding to the overlap region 512, the inferential modeling architecture 518 can more efficiently classify amino acid sequences than in situations where the inferential modeling architecture 518 is trained using amino acid sequences that do correspond to the overlap region 512. For example, in at least some situations, the amino acid sequence that correspond to the overlap region 512 may decrease the accuracy of the predictions produced by the inferential modeling architecture 518 with respect to the first classification 520 and the second classification 522.

Figure 6:
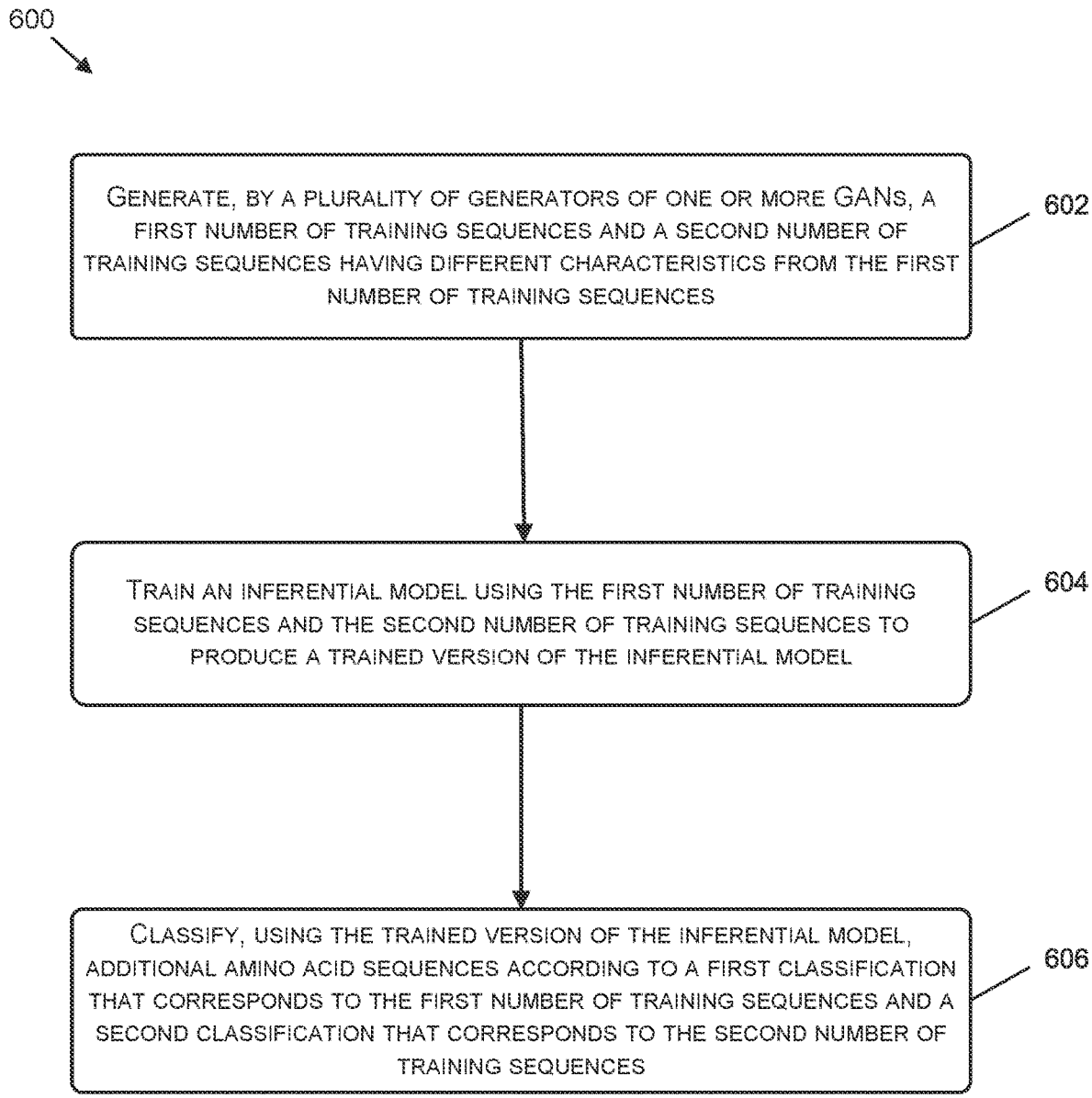
FIG. 6 is a flow diagram illustrating an example process to classify amino acid sequences using an inferential model that is trained using amino acid sequences produced by one or more generative adversarial networks, in accordance with one or more implementations.
Figure 7:
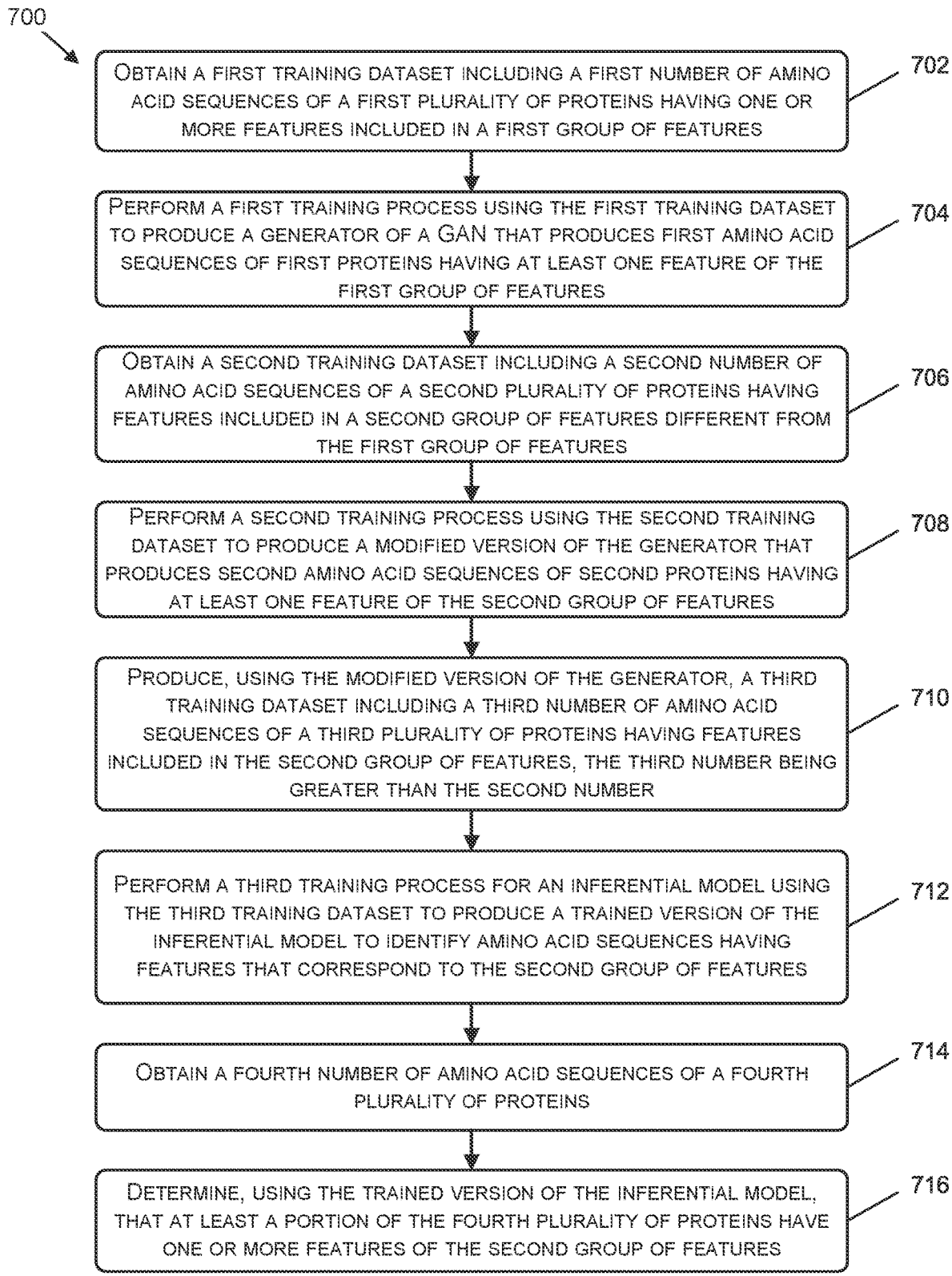
FIG. 7 is a flow diagram illustrating an example process to train an inferential model using amino acid sequences of proteins produced by one or more generative adversarial networks, in accordance with one or more implementations.

FIGS. 6 and 7 illustrate example processes for generating amino acid sequences of proteins using machine learning techniques. The example processes are illustrated as collections of blocks in logical flow graphs, which represent sequences of operations that can be implemented in hardware, software, or a combination thereof. The blocks are referenced by numbers. In the context of software, the blocks represent computer-executable instructions stored on one or more computer-readable media that, when executed by one or more processing units (such as hardware microprocessors), perform the recited operations. Generally, computer-executable instructions include routines, programs, objects, components, data structures, and the like that perform particular functions or implement particular data types. The order in which the operations are described is not intended to be construed as a limitation, and any number of the described blocks can be combined in any order and/or in parallel to implement the process.

FIG. 6 is a flow diagram illustrating an example process 600 to classify amino acid sequences using an inferential model that is trained using amino acid sequences produced by one or more generative adversarial networks, in accordance with one or more implementations. The process 600 can include, at 602, generating, by a plurality of generators of one or more generative adversarial networks, a first number of training sequences and a second number of training sequences having different characteristics from the first number of training sequences. The plurality of generators can include a first generator that produces the first number of training sequences and a second generator that produces the second number of training sequences. The first number of training sequences can include a first group of amino acid sequences of first proteins and the second number of training sequences can include a second group of amino acid sequences of second proteins. In one or more examples, the first proteins and the second proteins can include antibodies.

The characteristics of the first proteins and the characteristics of the second proteins can be different in that the first proteins have one or more characteristics that are not associated with the second proteins. The one or more characteristics that are different between the first proteins and the second proteins can include one or more biophysical properties and/or one or more structural features. For example, the first proteins can have one or more hydrophobic regions and a hydrophobic region can be absent from the second proteins. In one or more additional examples, the first proteins can comprise first antibodies having at least at a threshold amount of binding affinity for a first antigen and the second proteins can comprise second antibodies having at least a threshold amount of binding affinity for a second antigen that is different from the first antigen. Further, the one or more characteristics that are different between the first proteins and the second proteins can correspond to different sets of values for one or more biophysical properties and/or one or more structural features. To illustrate, the first proteins can have melting temperatures with a first range of values and the second proteins can have melting temperatures with a second range of values that is different from the first range of values. In addition, the first proteins can have negatively charged regions having a first range of sizes and the second proteins can have negatively charged regions having a second range of sizes different from the first range of sizes.

At 604, the process 600 can include training an inferential model using the first number of training sequences and the second number of training sequences to produce a trained version of the inferential model. In one or more examples, the inferential model can be trained to identify characteristics of proteins based on the amino acid sequences of proteins. To illustrate, the inferential model can be trained to identify amino acid sequences of proteins having one or more characteristics that correspond to the first number of training sequences and to identify amino acid sequences of proteins having one or more characteristics that correspond to the second number of training sequences.

In addition, the process 600 can include, at 606, classifying, using the trained version of the inferential model, additional amino acid sequences according to a first classification that corresponds to one or more features of the first number of training sequences and a second classification that corresponds to one or more features of the second number of training sequences. In one or more examples, the trained version of the inferential model can obtain an input sequence that includes an amino acid sequence of a protein. The trained version of the inferential model can analyze the amino acid sequence and determine a first probability of the amino acid sequence corresponding to the first classification and a second probability of the amino acid sequence corresponding to the second classification. In situations where the first probability satisfies a threshold probability, the trained version of the inferential model can determine that the amino acid sequence corresponds to the first classification. Additionally, in scenarios where the second probability satisfies a threshold probability, the trained version of the inferential model can determine that the amino acid sequence corresponds to the second classification. In further examples, the classification related to the higher of the first probability or the second probability can be associated with the amino acid sequence by the trained inferential modeling system.

FIG. 7 is a flow diagram illustrating an example process 700 to train an inferential model using amino acid sequences of proteins produced by one or more generative adversarial networks, in accordance with one or more implementations. At 702, the process 700 can include obtaining a first training dataset including a first number of amino acid sequences of a first plurality of proteins having one or more features included in a first group of features. In addition, at 704, the process 700 can include performing a first training process using the first training dataset to produce a generator of a generative adversarial network that produces first amino acid sequences having at least one feature of the first group of features. For example, the first training dataset can be provided to a challenging component of the generative adversarial network that is trained in conjunction with the generator. In various examples, the challenging component can evaluate the amino acid sequences produced by the generator in relation to the amino acid sequences included in the first training dataset.

After completing the training process to produce the generator of the generative adversarial network, the process 700 can include, at 706, obtaining a second training dataset including a second number of amino acid sequences of a second plurality of proteins having features included in a second group of features that is different from the first group of features. In one or more examples, the second training dataset can include a greater number of amino acid sequences of proteins having a subset of the features of a portion of the proteins corresponding to the amino acid sequences included in the first training dataset. For example, the first training dataset can include a first number of amino acid sequences of proteins having one or more negatively charged regions and the second training dataset can include a second number of amino acid sequences of proteins having one or more negatively charged regions that is greater than the first number of amino acid sequences. In one or more illustrative examples, the second number of amino acid sequences can be several times greater than the first number of amino acid sequences. Continuing with this example, the first training dataset can include a number of amino acid sequences of proteins that have one or more hydrophobic regions and a number of amino acid sequences of proteins that have one or more polar regions, while the second training dataset includes fewer amino acid sequences of proteins that include one or more polar regions and fewer amino acid sequences of proteins that include one or more hydrophobic regions than the first training dataset. In various examples, amino acid sequences of proteins having one or more polar regions and/or one or more hydrophobic regions may be absent from the second training dataset.

The process 700 can also include, at 708, performing a second training process using the second training dataset to produce a modified version of the generator that produces second amino acid sequences. The second training process can be part of a transfer learning process that is performed with respect to the generator to modify at least one of one or more parameters, one or more weights, or one or more functions executed by the generator to modify the structural features and/or biophysical properties of proteins corresponding to amino acid sequences produced by the generator. Additionally, at 710, the process 700 can include producing, using the modified version of the generator, a third training dataset that includes a third number of amino acid sequences of a third plurality of proteins having features included in the second group of features. In one or more illustrative examples, the third training dataset can include amino acid sequences of proteins having one or more negatively charged regions. The third number of proteins included in the third training dataset can be greater than the second number of proteins included in the second training dataset. In this way, the third training dataset can be used to train an inferential model that uses a greater amount of data for training than the amount of data used to train the generative adversarial network.

In one or more examples, amino acid sequences produced by the modified version of the generator can be filtered to generate the third training dataset. To illustrate, the amino acid sequences produced by the modified version of the generator can be analyzed with respect to one or more criteria to determine whether respective amino acid sequences produced by the modified version of the generator are to be included in the third training dataset. For example, the amino acid sequences produced by the modified version of the generator can be analyzed to identify proteins having one or more structural features and/or one or more biophysical properties that correspond to classifications that are to be used by the inferential model. In one or more illustrative examples, the amino acid sequences produced by the modified version of the generator can be analyzed to identify proteins having one or more ranges of values of one or more biophysical properties and/or one or more ranges of values of one or more structural features.

Additionally, the process 700 can include, at 712, performing a third training process for an inferential model using the third training dataset to produce a trained version of the inferential model. The trained version of the inferential model can identify amino acid sequences of proteins having one or more classifications. In various examples, at least one of the classifications can correspond to one or more of the second group of features that characterize proteins of the third training dataset. For example, in situations where the third training dataset includes amino acid sequences of proteins including one or more polar regions having a range of sizes, the trained version of the inferential model can determine a probability of additional amino acid sequences including one or more polar regions having the range of sizes. Additionally, the third training process can include providing additional training datasets for the inferential model where the additional training datasets include amino acid sequences of proteins having different characteristics from each other additional training dataset and from the third training dataset. In one or more illustrative examples, a number of training datasets used to train the inferential model can include amino acid sequences of proteins having different structural features. To illustrate, the inferential model can be trained using a training dataset that includes amino acid sequences of proteins having one or more polar regions and an additional training dataset that includes amino acid sequences of proteins having one or more hydrophobic regions. Accordingly, the trained version of the inferential model can determine probabilities that amino acid sequences correspond to proteins having one or more hydrophobic regions and probabilities that amino acid sequences correspond to proteins having one or more polar regions. In one or more additional illustrative examples, the trained version of the inferential model can determine probabilities of amino acid sequences corresponding to proteins having a number of ranges of values for one or more structural features and/or values for one or more biophysical properties. In one or more scenarios, the trained version of the inferential model can determine probabilities of amino acid sequences of proteins having a first range of values for solubility in water and probabilities of amino acid sequences of proteins having a second range of values for solubility in water. In these situations, the training of the inferential model can be performed using a training dataset that includes amino acid sequences of proteins having values of solubility in water included in the first range of values and an additional training dataset that includes amino acid sequences of proteins having values of solubility in water included in the second range of values.

Further, at 714, the process 700 can include obtaining a fourth number of amino acid sequences of a fourth plurality of proteins. The fourth number of amino acid sequences can include input sequences that are to be classified by the trained version of the inferential model. The process 700 can also include, at 716, determining, using the trained version of the inferential model, that at least a portion of the fourth plurality of proteins have one or more features of the second group of features. In one or more examples, the trained version of the inferential model can determine a probability that an amino acid sequence included in the fourth number of amino acid sequences corresponds to a protein having a feature included in the second group of features. In situations where the probability is above a threshold probability, the trained version of the inferential model can determine a classification for the amino acid sequence that corresponds to the feature. The feature can include a structural feature, a range of values of a structural feature, a biophysical property, a range of values of the biophysical property, or one or more combinations thereof.

Figure 8:
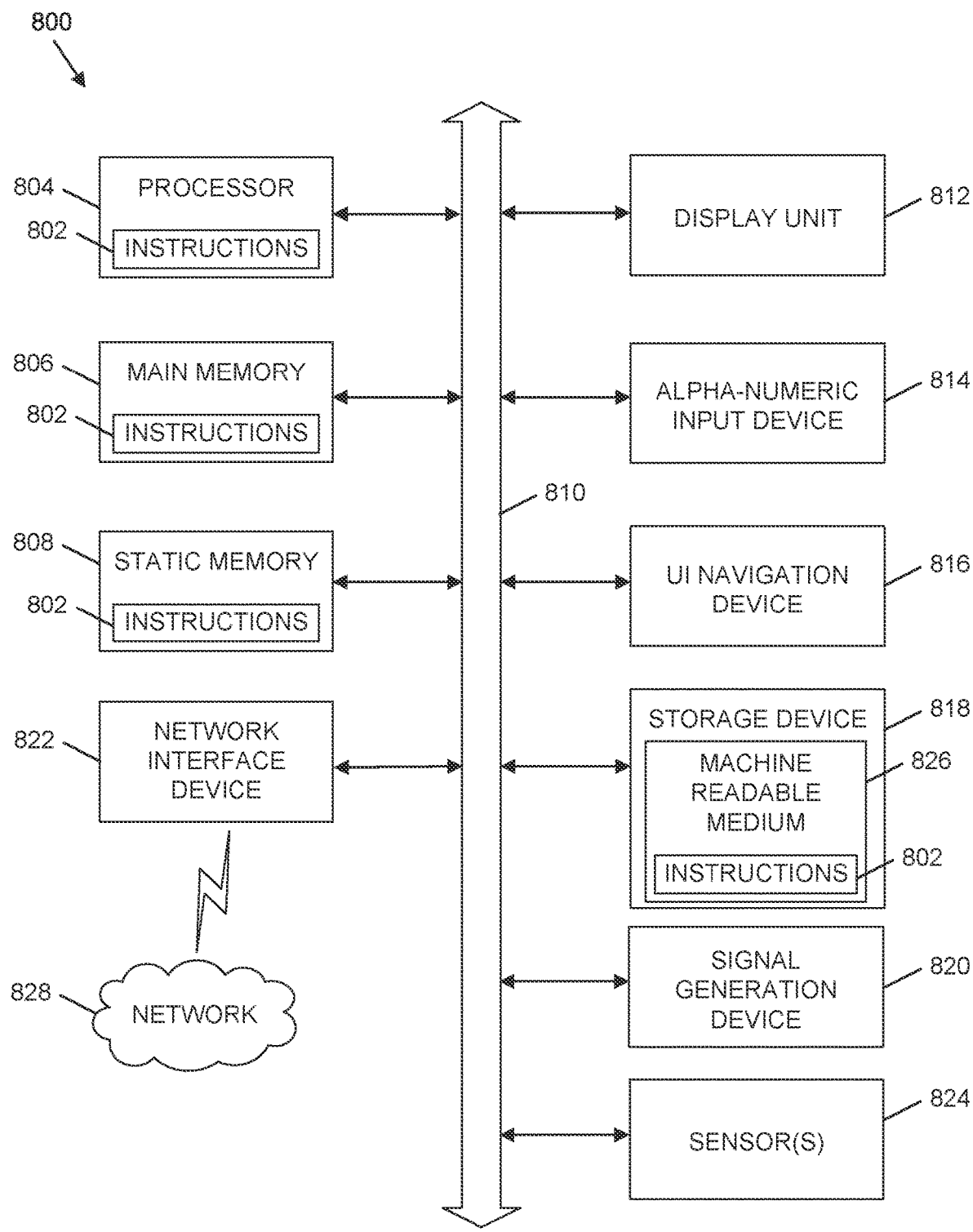
FIG. 8 illustrates a diagrammatic representation of a machine in the form of a computer system within which a set of instructions may be executed for causing the machine to perform any one or more of the methodologies discussed herein, according to one or more implementations.

FIG. 8 illustrates a diagrammatic representation of a machine 800 in the form of a computer system within which a set of instructions may be executed for causing the machine 800 to perform any one or more of the methodologies discussed herein, according to an example, according to an example implementation. Specifically, FIG. 8 shows a diagrammatic representation of the machine 800 in the example form of a computer system, within which instructions 802 (e.g., software, a program, an application, an applet, an app, or other executable code) for causing the machine 800 to perform any one or more of the methodologies discussed herein may be executed. For example, the instructions 802 may cause the machine 800 to implement the frameworks 100, 200, 300, 400, 500 described with respect to FIGS. 1, 2, 3, 4, and 5, respectively, and to execute the processes 600, 700 described with respect to FIGS. 6 and 7, respectively.

The instructions 802 transform the general, non-programmed machine 800 into a particular machine 800 programmed to carry out the described and illustrated functions in the manner described. In alternative implementations, the machine 800 operates as a standalone device or may be coupled (e.g., networked) to other machines. In a networked deployment, the machine 800 may operate in the capacity of a server machine or a client machine in a server-client network environment, or as a peer machine in a peer-to-peer (or distributed) network environment. The machine 800 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 802, sequentially or otherwise, that specify actions to be taken by the machine 800. Further, while only a single machine 800 is illustrated, the term "machine" shall also be taken to include a collection of machines 800 that individually or jointly execute the instructions 802 to perform any one or more of the methodologies discussed herein.

Examples of machine 800 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein.

In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can comprise dedicated circuitry or logic that is specifically configured to perform one or more techniques such as discussed above, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits comprise a general-purpose processor configured via software, the general-purpose processor can be configured as respective different circuits at different times. Software can accordingly configure a processor, for example, to constitute a particular circuit at one instance of time and to constitute a different circuit at a different instance of time.

In an example, circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In implementations in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service"

(SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example implementations (e.g., apparatus, systems, or methods) can be implemented in digital electronic circuitry, in computer hardware, in firmware, in software, or in any combination thereof. Example implementations can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In implementations deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 800) and software architectures that can be deployed in example implementations.

In an example, the machine 800 can operate as a stand-alone device or the machine 800 can be connected (e.g., networked) to other machines.

In a networked deployment, the machine 800 can operate in the capacity of either a server or a client machine in server-client network environments. In an example, machine 800 can act as a peer machine in peer-to-peer (or other distributed) network environments. The machine 800 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 800. Further, while only a single machine 800 is illustrated, the term "computing device" shall also be taken to include any collection of machines that individually or jointly execute a set (or multiple sets) of instructions to perform any one or more of the methodologies discussed herein.

Example machine 800 can include a processor 804 (e.g., a central processing unit CPU), a graphics processing unit (GPU) or both), a main memory 806 and a static memory 808, some or all of which can communicate with each other via a bus 810. The machine 800 can further include a display unit 812, an alphanumeric input device 814 (e.g., a keyboard), and a user interface (UI) navigation device 816 (e.g., a mouse). In an example, the display unit 812, input device 814 and LI navigation device 816 can be a touch screen display. The machine 800 can additionally include a storage device (e.g., drive unit) 818, a signal generation device 820 (e.g., a speaker), a network interface device 822, and one or more sensors 824, such as a global positioning system (GPS) sensor, compass, accelerometer, or another sensor.

The storage device 818 can include a machine readable medium 826 on which is stored one or more sets of data structures or instructions 802 (e.g., software) embodying or utilized by any one or more of the methodologies or functions described herein. The instructions 802 can also reside, completely or at least partially, within the main memory 806, within static memory 808, or within the processor 804 during execution thereof by the machine 800. In an example, one or any combination of the processor 804, the main memory 806, the static memory 808, or the storage device 818 can constitute machine readable media.

While the machine readable medium 826 is illustrated as a single medium, the term "machine readable medium" can include a single medium or multiple media (e.g., a centralized or distributed database, and/or associated caches and servers) that configured to store the one or more instructions 802. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine-readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 802 can further be transmitted or received over a communications network 828 using a transmission medium via the network interface device 822 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

EXAMPLE IMPLEMENTATIONS

Implementation 1. A method comprising: obtaining, by a computing system including one or more computing devices having one or more processors and memory, a first training dataset including a first number of amino acid sequences of a first plurality of proteins, individual first proteins of the first plurality of proteins having one or more first features of a first group of features; performing, by the computing system, a first training process using the first training dataset to produce a generator of a generative adversarial network that produces first additional amino acid sequences of first additional proteins having at least one first feature of the first group of features; obtaining, by the computing system, a second training dataset including a second number of amino acid sequences of a second plurality of proteins, individual second proteins of the second plurality of proteins having one or more second features of a second group of features, the second group of features being different from the first group of features; performing by the computing system, a second training process using the second training dataset to produce a modified version of the generator that produces second additional amino acid sequences of second additional proteins having at least one second feature of the one or more second features; producing, by the computing system and using the modified version of the generator, a third number of amino acid sequences of a third plurality of proteins, individual third proteins of the third plurality of proteins having at least a portion of the one or more second features, and the third number of amino acid sequences being greater than the second number of amino acid sequences; performing, by the computing system, a third training process for an inferential model using at least a portion of the third number of amino acid sequences at a third training dataset to produce a trained version of the inferential model, the trained version of the inferential model to identify amino acid sequences having features that correspond to at least a portion of the second group of features; obtaining, by the computing system, a fourth number of amino acid sequences of a fourth plurality of proteins; and determining, by the computing system and using the trained version of the inferential model, that at least a portion of the fourth plurality of proteins have one or more second features of the second group of features.

Implementation 2. The method of implementation 1, wherein the second group of features includes a first feature of the first group of features and an additional first feature of the first group of features is absent from the second group of features.

Implementation 3. The method of implementation 1 or 2, wherein the second plurality of proteins have a first distribution of values for a second feature of the second group of features and the second additional proteins have a second distribution of values for the second feature that corresponds to the first distribution of values.

Implementation 4. The method of any one of implementations 1 to 3, wherein the second training dataset includes a greater number of amino acid sequences corresponding to proteins having a second feature of the second group of features than a number of amino sequences included in the first training dataset.

Implementation 5. The method of any one of implementations 1 to 4, further comprising: determining, by the computing system and using the inferential model, a first probability that a fourth amino acid sequence of the fourth number of amino acid sequences corresponds to a protein having a first classification; and determining, by the computing system and using the inferential model, a second probability that the fourth amino acid sequence corresponds to a protein having a second classification.

Implementation 6. The method of implementation 5, further comprising: determining, by the computing system, that the first probability satisfies a threshold probability; and determining, by the computing system, that the fourth amino acid sequence is classified according to the first classification.

Implementation 7. The method of implementation 5 or 6, wherein the first classification corresponds to proteins having at least one of a first structural feature or a first biophysical property and the second classification corresponds to proteins having at least one of a second structural feature or a second biophysical property.

Implementation 8. The method of implementation 5 or 6, wherein the first classification corresponds to a first range of values of a structural property or a first range of values of a biophysical property and the second classification corresponds to a second range of values of the structural property or a second range of values of the biophysical property.

Implementation 9. The method of any one of implementations 1 to 8, further comprising: analyzing, by the computing system, an amino acid sequence included in the third number of amino acid sequences to determine a probability that a third protein corresponding to the amino acid sequences has a value of a structural feature included in the second group of features that is within a specified range of values; determining, by the computing system, that the probability corresponds to a threshold probability; and determining, by the computing system, that the amino acid sequence is to be included in the third training dataset.

Implementation 10. A computing system comprising: one or more hardware processors; and one or more non-transitory computer readable media storing computer-executable instructions that, when executed by the one or more hardware processors, cause the one or more processor to perform operations comprising: obtaining a first training dataset including a first number of amino acid sequences of a first plurality of proteins, individual first proteins of the first plurality of proteins having one or more first features of a first group of features; performing a first training process using the first training dataset to produce a generator of a generative adversarial network that produces first additional amino acid sequences of first additional proteins having at least one first feature of the first group of features; obtaining a second training dataset including a second number of amino acid sequences of a second plurality of proteins, individual second proteins of the second plurality of proteins having one or more second features of a second group of features, the second group of features being different from the first group of features; performing a second training process using the second training dataset to produce a modified version of the generator that produces second additional amino acid sequences of second additional proteins having at least one second feature of the one or more second features; producing using the modified version of the generator, a third number of amino acid sequences of a third plurality of proteins, individual third proteins of the third plurality of proteins having at least a portion of the one or more second features, and the third number of amino acid sequences being greater than the second number of amino acid sequences; performing a third training process for an inferential model using at least a portion of the third number of amino acid sequences at a third training dataset to produce a trained version of the inferential model, the trained version of the inferential model to identify amino acid sequences having features that correspond to at least a portion of the second group of features; obtaining a fourth number of amino acid sequences of a fourth plurality of proteins; and determining, using the trained version of the inferential model, that at least a portion of the fourth plurality of proteins have one or more second features of the second group of features.

Implementation 11. The computing system of implementation 10, wherein the second group of features includes a first feature of the first group of features and an additional first feature of the first group of features is absent from the second group of features.

Implementation 12. The computing system of implementation 10 or 11, wherein the second plurality of proteins have a first distribution of values for a second feature of the second group of features and the second additional proteins have a second distribution of values for the second feature that corresponds to the first distribution of values.

Implementation 13. The computing system of any one of implementations 10 to 12, wherein the second training dataset includes a greater number of amino acid sequences corresponding to proteins having a second feature of the second group of features than a number of amino sequences included in the first training dataset.

Implementation 14. The computing system of any one of implementations 10 to 13, wherein the one or more non-transitory computer readable media store additional computer-executable instructions that, when executed by the one or more hardware processors, cause the one or more processor to perform additional operations comprising: determining, using the inferential model, a first probability that a fourth amino acid sequence of the fourth number of amino acid sequences corresponds to a protein having a first classification; and determining, using the inferential model, a second probability that the fourth amino acid sequence corresponds to a protein having a second classification.

Implementation 15. The computing system of implementation 14, wherein the one or more non-transitory computer readable media store additional computer-executable instructions that, when executed by the one or more hardware processors, cause the one or more processor to perform additional operations comprising: determining that the first probability satisfies a threshold probability; and determining that the fourth amino acid sequence is classified according to the first classification.

Implementation 16. The computing system of implementation 14 or 15, wherein the first classification corresponds to proteins having at least one of a first structural feature or a first biophysical property and the second classification corresponds to proteins having at least one of a second structural feature or a second biophysical property.

Implementation 17. The computing system of implementation 14 or 15, wherein the first classification corresponds to a first range of values of a structural property or a first range of values of a biophysical property and the second classification corresponds to a second range of values of the structural property or a second range of values of the biophysical property.

Implementation 18. The computing system of any one of implementations 10 to 17, wherein the one or more non-transitory computer readable media store additional computer-executable instructions that, when executed by the one or more hardware processors, cause the one or more processor to perform additional operations comprising: analyzing an amino acid sequence included in the third number of amino acid sequences to determine a probability that a third protein corresponding to the amino acid sequences has a value of a structural feature included in the second group of features that is within a specified range of values; determining that the probability corresponds to a threshold probability; and determining that the amino acid sequence is to be included in the third training dataset.

Implementation 19. A computing system comprising: one or more hardware processors; and one or more non-transitory computer readable media storing computer-executable instructions that, when executed by the one or more hardware processors, cause the one or more processor to perform operations comprising: generating, by a plurality of generators of one or more generative adversarial networks, a first number of amino acid sequences, a first portion of the first number of amino acid sequences corresponding to a first group of antibodies having first values for a feature of antibodies and a second portion of the first number of amino acid sequences corresponding to a second group of antibodies having second values for the feature that are different from the first values; training an inferential model using the first number of amino acid sequences to produce a trained version of the inferential model; and classifying, using the trained version of the inferential model, individual amino acid sequences of a second number of amino acid sequences as being included in the first group of antibodies or the second group of antibodies.

Implementation 20. The computing system of implementation 19, wherein the first portion of the first number of amino acid sequences corresponds to a first training dataset for the inferential model and the second portion of the first number of amino acid sequences corresponds to a second training dataset for the inferential model.

Implementation 21. The computing system of implementation 20, wherein the one or more generative adversarial networks includes a first generative adversarial network to generate the first portion of the first number of amino acid sequences included in the first training dataset and a second generative adversarial network to generate the second portion of the first number of amino acid sequences included in the second training dataset.

Implementation 22. The computing system of implementation 21, wherein the one or more non-transitory computer readable media store additional computer-executable instructions that, when executed by the one or more hardware processors, cause the one or more processor to perform additional operations comprising: training a first generating component of the first generative adversarial network using a first additional training dataset, the first additional training dataset including first amino acid sequences of antibodies that have at least a portion of the first values for the feature; and training a second generating component of the second generative adversarial network using a second additional training dataset, the second additional training dataset including second amino acid sequences of antibodies that have at least a portion of the second values for the feature.

Implementation 23. The computing system of implementation 19, wherein: the first number of amino acid sequences includes a first distribution indicating one or more amino acid sequences having respective values for the feature that are included in the first values and a second distribution indicating one or more additional amino acid sequences having respective additional values for the feature that are included in the second values; and the first distribution and the second distribution have an overlap region that at least one amino acid sequence included in the first distribution that has a same value for the feature as at least one amino acid sequence included in the second distribution.

Implementation 24. The computing system of implementation 23, wherein the one or more non-transitory computer readable media store additional computer-executable instructions that, when executed by the one or more hardware processors, cause the one or more processor to perform additional operations comprising: determining a first training dataset for the inferential model that includes a portion of the first distribution that does not include amino acid sequences of the first portion of the first number of amino acids included in the overlap region; and determining a second training dataset for the inferential model that includes a portion of the second distribution that does not include amino acids of the second portion of the first number of amino acids included in the overlap region.

Implementation 25. The computing system of any one of implementations 19 to 24, wherein the one or more non-transitory computer readable media store additional computer-executable instructions that, when executed by the one or more hardware processors, cause the one or more processor to perform additional operations comprising: generating, by the inferential model, classification data for the second number of amino acid sequences, the classification data indicating a first group of the second number of amino acid sequences corresponding to a first classification and a second group of the second number of amino acid sequences corresponding to a second classification, the first classification corresponding to the first values for the feature and the second classification corresponding to the second values for the feature; providing the classification data to a regression model; and determining, using the regression model and based on the classification data, a probability of at least a portion of the second number of amino acid sequences having a biophysical property.

Implementation 26. The computing system of any one of implementations 19 to 25, wherein the one or more non-transitory computer readable media store additional computer-executable instructions that, when executed by the one or more hardware processors, cause the one or more processor to perform additional operations comprising: generating, using a light chain generating component of a generative adversarial network of the one or more generative adversarial networks, a first amino acid sequence that corresponds to a light chain of an antibody; generating, using a heavy chain generating component of the generative adversarial network, a second amino acid sequence that corresponds to a heavy chain of the antibody; and combining the first amino acid sequence and the second amino acid sequence to produce a third amino acid sequence that is included in the first number of amino acid sequences.

Implementation 27. The computing system of any one of implementations 19 to 26, wherein the feature includes a number of amino acids included in a hydrophobic region of an antibody, a number of amino acids included in a positively charged region of an antibody, a number of amino acids included in a negatively charged region of an antibody, a number of amino acids included in a polar region of an antibody, a number of amino acids included in an uncharged region of an antibody, a level of expression of an antibody, a melting temperature of an antibody, a measure of solubility of an antibody in water, a measure of acidity of an antibody, a measure of viscosity of an antibody, a measure of immunogenicity of an antibody, or a level of self-aggregation of an antibody.

Implementation 28. A method comprising: generating, by a plurality of generators of one or more generative adversarial networks, a first number of amino acid sequences, a first portion of the first number of amino acid sequences corresponding to a first group of antibodies having first values for a feature of antibodies and a second portion of the first number of amino acid sequences corresponding to a second group of antibodies having second values for the feature that are different from the first values; training an inferential model using the first number of amino acid sequences to produce a trained version of the inferential model; and classifying, using the trained version of the inferential model, individual amino acid sequences of a second number of amino acid sequences as being included in the first group of antibodies or the second group of antibodies.

Implementation 29. The method of implementation 28, wherein the first portion of the first number of amino acid sequences corresponds to a first training dataset for the inferential model and the second portion of the first number of amino acid sequences corresponds to a second training dataset for the inferential model.

Implementation 30. The method of implementation 29, wherein the one or more generative adversarial networks includes a first generative adversarial network to generate the first portion of the first number of amino acid sequences included in the first training dataset and a second generative adversarial network to generate the second portion of the first number of amino acid sequences included in the second training dataset.

Implementation 31. The method of implementation 30, comprising: training a first generating component of the first generative adversarial network using a first additional training dataset, the first additional training dataset including first amino acid sequences of antibodies that have at least a portion of the first values for the feature; and training a second generating component of the second generative adversarial network using a second additional training dataset, the second additional training dataset including second amino acid sequences of antibodies that have at least a portion of the second values for the feature.

Implementation 32. The method of implementation 28, wherein: the first number of amino acid sequences includes a first distribution indicating one or more amino acid sequences having respective values for the feature that are included in the first values and a second distribution indicating one or more additional amino acid sequences having respective additional values for the feature that are included in the second values; and the first distribution and the second distribution have an overlap region that at least one amino acid sequence included in the first distribution that has a same value for the feature as at least one amino acid sequence included in the second distribution.

Implementation 33. The method of implementation 32, comprising: determining a first training dataset for the inferential model that includes a portion of the first distribution that does not include amino acid sequences of the first portion of the first number of amino acids included in the overlap region; and determining a second training dataset for the inferential model that includes a portion of the second distribution that does not include amino acids of the second portion of the first number of amino acids included in the overlap region.

Implementation 34. The method of any one of implementations 28 to 33, comprising: generating, by the inferential model, classification data for the second number of amino acid sequences, the classification data indicating a first group of the second number of amino acid sequences corresponding to a first classification and a second group of the second number of amino acid sequences corresponding to a second classification, the first classification corresponding to the first values for the feature and the second classification corresponding to the second values for the feature; providing the classification data to a regression model; and determining, using the regression model and based on the classification data, a probability of at least a portion of the second number of amino acid sequences having a biophysical property.

Implementation 35. The method of any one of implementations 28 to 34, comprising: generating, using a light chain generating component of a generative adversarial network of the one or more generative adversarial networks, a first amino acid sequence that corresponds to a light chain of an antibody; generating, using a heavy chain generating component of the generative adversarial network, a second amino acid sequence that corresponds to a heavy chain of the antibody; and combining the first amino acid sequence and the second amino acid sequence to produce a third amino acid sequence that is included in the first number of amino acid sequences.

Implementation 36. The method of any one of implementations 28 to 35, wherein the feature includes a number of amino acids included in a hydrophobic region of an antibody, a number of amino acids included in a positively charged region of an antibody, a number of amino acids included in a negatively charged region of an antibody, a number of amino acids included in a polar region of an antibody, a number of amino acids included in an uncharged region of an antibody, a level of expression of an antibody, a melting temperature of an antibody, a measure of solubility of an antibody in water, a measure of acidity of an antibody, a measure of viscosity of an antibody, a measure of immunogenicity of an antibody, or a level of self-aggregation of an antibody.

What is claimed is:

1. A method comprising:
    obtaining, by a computing system including one or more computing devices having one or more processors and memory, a first training dataset including first amino acid sequences of first proteins, individual first proteins have one or more first features of a first group of features;
    performing, by the computing system, a first training process that includes:
        encoding individual first amino acid sequences as a matrix according to amino acids located at positions of individual first proteins to produce a plurality of matrices corresponding to encoded versions of the first amino acid sequences;
        generating input data using a random number generator or pseudo-random number generator, wherein the input data is provided to a generating component of a generative adversarial network;
        producing, by the generating component and based on the input data, generated sequences that correspond to additional amino acid sequences, wherein the generated sequences are represented as vectors indicating amino acids located at a number of positions;
        computationally analyzing, by a challenging component of the generative adversarial network and implementing a distance function, the vectors corresponding to the generated sequences and the plurality of matrices corresponding to the encoded versions of the first amino acid sequences to produce challenging component output indicating differences between the generated sequences and the first amino acid sequences; and
        modifying, based on the challenging component output, at least one of one or more parameters, one or more weights, or one or more variables of one or more machine learning models of the generating component until a loss function of the generating component is minimized to produce a trained version of the generating component;
    obtaining, by the computing system, a second training dataset including second amino acid sequences of second proteins, individual second proteins having one or more second features of a second group of features, the second group of features being different from the first group of features;
    performing by the computing system, transfer learning with respect to the trained version of the generating component based on the second training dataset, wherein the transfer learning includes modifying at least one of the one or more parameters, the one or more weights, or the one or more variables of the one or more machine learning models of the generating component in response to minimizing the loss function of trained version of the generating component with respect to the second training dataset to produce a modified version of the generating component, wherein the modified version of the generating component produces second additional amino acid sequences of second additional proteins having at least one second feature of the one or more second features;
    producing, by the modified version of the generating component as implemented by the computing system, third amino acid sequences of third proteins, individual third proteins having at least a portion of the one or more second features, and the third amino acid sequences being greater in number than the second amino acid sequences;
    performing, by the computing system, an additional training process for an inferential model using a third training dataset that includes at least a portion of the third amino acid sequences to produce a trained version of the inferential model, the trained version of the inferential model to classify amino acid sequences as having features that correspond to at least a portion of the second group of features;
    obtaining, by the computing system, fourth amino acid sequences of fourth proteins; and
    determining, by the trained version of the inferential model as implemented by the computing system, one or more classifications for the fourth proteins, the one or more classifications indicating at least one or more structural features of the fourth proteins.

2. The method of claim 1, wherein the second group of features includes a first feature of the first group of features and an additional first feature of the first group of features is absent from the second group of features.

3. The method of claim 1, wherein the second proteins have a first distribution of values for a second feature of the second group of features and the second additional proteins have a second distribution of values for the second feature.

4. The method of claim 1, wherein the second training dataset includes a greater number of amino acid sequences corresponding to proteins having a second feature of the second group of features than a number of amino sequences included in the first training dataset.

5. The method of claim 1, further comprising:
determining, by the inferential model as implemented by the computing system, a first probability that a fourth amino acid sequence of the fourth of amino acid sequences corresponds to a protein having a first classification; and
determining, by the inferential model as implemented by computing system, a second probability that the fourth amino acid sequence corresponds to a protein having a second classification.

6. The method of claim 5, further comprising:
determining, by the computing system, that the first probability satisfies a threshold probability; and
determining, by the computing system, that the fourth amino acid sequence is classified according to the first classification.

7. The method of claim 5, wherein the first classification corresponds to proteins having at least one of a first structural feature or a first biophysical property and the second classification corresponds to proteins having at least one of a second structural feature or a second biophysical property.

8. The method of claim 5, wherein the first classification corresponds to a first range of values of a structural property or a first range of values of a biophysical property and the second classification corresponds to a second range of values of the structural property or a second range of values of the biophysical property.

9. The method of claim 1, further comprising:
analyzing, by the computing system, a third amino acid sequence included in the third amino acid sequences to determine a probability that a third protein corresponding to the third amino acid sequence has a value of a structural feature included in the second group of features that is within a specified range of values;
determining, by the computing system, that the probability corresponds to a threshold probability; and
determining, by the computing system, that the third amino acid sequence is to be included in the third training dataset.

10. A system comprising:
one or more hardware processors; and
one or more non-transitory computer readable media storing computer-executable instructions that, when executed by the one or more hardware processors, cause the one or more hardware processors to perform operations comprising:
obtaining a first training dataset including first amino acid sequences of first proteins, individual first proteins having one or more first features of a first group of features;
performing a first training process that includes:
encoding individual first amino acid sequences as a matrix according to amino acids located at positions of individual first proteins to produce a plurality of matrices corresponding to encoded versions of the first amino acid sequences;
generating input data using a random number generator or pseudo-random number generator, wherein the input data is provided to a generating component of a generative adversarial network;
producing, by the generating component and based on the input data, generated sequences that correspond to additional amino acid sequences, wherein the generated sequences are represented as vectors indicating amino acids located at a number of positions;
computationally analyzing, by a challenging component of the generative adversarial network and implementing a distance function, the vectors corresponding to the generated sequences and the plurality of matrices corresponding to the encoded versions of the first amino acid sequences to produce challenging component output indicating differences between the generated sequences and the first amino acid sequences; and
modifying, based on the challenging component output, at least one of one or more parameters, one or more weights, or one or more variables of one or more machine learning models of the generating component until a loss function of the generating component is minimized to produce a trained version of the generating component;
obtaining a second training dataset including second amino acid sequences of second proteins, individual second proteins having one or more second features of a second group of features, the second group of features being different from the first group of features;
performing transfer learning with respect to the trained version of the generating component based on the second training dataset, wherein the transfer learning includes modifying at least one of the one or more parameters, the one or more weights, or the one or more variables of the one or more machine learning models of the generating component in response to minimizing the loss function of trained version of the generating component with respect to the second training dataset to produce a modified version of the generating component, wherein the generating component produces second additional amino acid sequences of second additional proteins having at least one second feature of the one or more second features;
producing, using the modified version of the generating component, third amino acid sequences of third proteins, individual third proteins having at least a portion of the one or more second features, and the third amino acid sequences being greater in number than the second amino acid sequences;
performing an additional training process for an inferential model using a third training dataset that includes at least a portion of the third amino acid sequences to produce a trained version of the inferential model, the trained version of the inferential model to classify amino acid sequences as having features that correspond to at least a portion of the second group of features;
obtaining fourth amino acid sequences of fourth proteins; and
determining, by the trained version of the inferential model, one or more classifications for the fourth proteins, the one or more classifications indicating at least one or more structural features of the fourth proteins.

11. The system of claim 10, wherein the second group of features includes a first feature of the first group of features and an additional first feature of the first group of features is absent from the second group of features.

12. The system of claim 10, wherein the second proteins have a first distribution of values for a second feature of the second group of features and the second additional proteins have a second distribution of values for the second feature.

13. The system of claim 10, wherein the second training dataset includes a greater number of amino acid sequences corresponding to proteins having a second feature of the second group of features than a number of amino sequences included in the first training dataset.

14. The system of claim 10, wherein the one or more non-transitory computer readable media store additional computer-executable instructions that, when executed by the one or more hardware processors, cause the one or more hardware processors to perform additional operations comprising:
 determining, by the inferential model, a first probability that a fourth amino acid sequence of the fourth amino acid sequences corresponds to a protein having a first classification; and
 determining, by the inferential model, a second probability that the fourth amino acid sequence corresponds to a protein having a second classification.

15. The system of claim 14, wherein the one or more non-transitory computer readable media store additional computer-executable instructions that, when executed by the one or more hardware processors, cause the one or more hardware processors to perform additional operations comprising:
 determining that the first probability satisfies a threshold probability; and
 determining that the fourth amino acid sequence is classified according to the first classification.

16. The system of claim 14, wherein the first classification corresponds to proteins having at least one of a first structural feature or a first biophysical property and the second classification corresponds to proteins having at least one of a second structural feature or a second biophysical property.

17. The system of claim 14, wherein the first classification corresponds to a first range of values of a structural property or a first range of values of a biophysical property and the second classification corresponds to a second range of values of the structural property or a second range of values of the biophysical property.

18. The system of claim 10, wherein the one or more non-transitory computer readable media store additional computer-executable instructions that, when executed by the one or more hardware processors, cause the one or more hardware processors to perform additional operations comprising:
 analyzing a third amino acid sequence included in the third amino acid sequences to determine a probability that a third protein corresponding to the third amino acid sequence has a value of a structural feature included in the second group of features that is within a specified range of values;
 determining that the probability corresponds to a threshold probability; and
 determining that the third amino acid sequence is to be included in the third training dataset.

19. One or more non-transitory computer-readable storage media storing computer-executable instructions that, when executed by one or more hardware processors, cause the one or more hardware processors to perform operations comprising:
 obtaining a first training dataset including first amino acid sequences of first proteins, individual first proteins having one or more first features of a first group of features;
 performing a first training process using the first training dataset that includes:
  encoding individual first amino acid sequences as a matrix according to amino acids located at positions of individual first proteins to produce a plurality of matrices corresponding to encoded versions of the first amino acid sequences;
  generating input data using a random number generator or pseudo-random number generator, wherein the input data is provided to a generating component of a generative adversarial network;
  producing, by the generating component and based on the input data, generated sequences that correspond to additional amino acid sequences, wherein the generated sequences are represented as vectors indicating amino acids located at a number of positions;
  computationally analyzing, by a challenging component of the generative adversarial network and implementing a distance function, the vectors corresponding to the generated sequences and the plurality of matrices corresponding to the encoded versions of the first amino acid sequences to produce challenging component output indicating differences between the generated sequences and the first amino acid sequences; and
  modifying, based on the challenging component output, at least one of one or more parameters, one or more weights, or one or more variables of one or more machine learning models of the generating component until a loss function of the generating component is minimized to produce a trained version of the generating component;
 obtaining a second training dataset including second amino acid sequences of second proteins, individual second proteins of the second proteins having one or more second features of a second group of features, the second group of features being different from the first group of features;
 performing transfer learning with respect to the trained version of the generating component based on the second training dataset, wherein the transfer learning includes modifying at least one of the one or more parameters, the one or more weights, or the one or more variables of the one or more machine learning models of the generating component in response to minimizing the loss function of trained version of the generating component with respect to the second training dataset produce a modified version of the generating component, wherein the generating component produces second additional amino acid sequences of second additional proteins having at least one second feature of the one or more second features;
 producing, by the modified version of the generating component, third amino acid sequences of third proteins, individual third proteins having at least a portion of the one or more second features, and the third amino acid sequences being greater in number than the second amino acid sequences;
 performing an additional training process for an inferential model using a third training dataset that includes at least a portion of the third amino acid sequences to produce a trained version of the inferential model, the trained version of the inferential model to classify amino acid sequences having features that correspond to at least a portion of the second group of features;

obtaining fourth amino acid sequences of fourth proteins; and determining, by the trained version of the inferential model, one or more classifications for the fourth proteins, the one or more classifications indicating at least one or more structural features of the fourth proteins.

20. The one or more non-transitory computer-readable storage media of claim 19, storing additional computer-readable instructions that when executed by the one or more hardware processors, cause the one or more hardware processors to perform additional operations comprising:

determining, by the inferential model, a first probability that a fourth amino acid sequence of the fourth amino acid sequences corresponds to a protein having a first classification;

determining, by the inferential model, a second probability that the fourth amino acid sequence corresponds to a protein having a second classification;

determining that the first probability satisfies a threshold probability; and determining that the fourth amino acid sequence is classified according to the first classification, wherein the first classification corresponds to a first range of values of a structural property or a first range of values of a biophysical property and the second classification corresponds to a second range of values of the structural property or a second range of values of the biophysical property.

* * * * *